US008133692B2

(12) United States Patent
Jove et al.

(10) Patent No.: US 8,133,692 B2
(45) Date of Patent: Mar. 13, 2012

(54) METHODS OF PREDICTING RESPONSIVENESS TO CHEMOTHERAPEUTIC AGENTS AND SELECTING TREATMENTS

(75) Inventors: Richard Jove, Glendora, CA (US); Susan E. Minton, Tampa, FL (US); Carlos A. Muro-Cacho, Tampa, FL (US); Daniel Sullivan, Lutz, FL (US); Eric Bruce Haura, Tampa, FL (US); Gerold Bepler, Tierra Verde, FL (US)

(73) Assignee: University of South Florida, Tampa, FL (US)

( * ) Notice: Subject to any disclaimer, the term of this patent is extended or adjusted under 35 U.S.C. 154(b) by 205 days.

(21) Appl. No.: 11/490,316

(22) Filed: Jul. 20, 2006

(65) Prior Publication Data
US 2007/0031871 A1    Feb. 8, 2007

Related U.S. Application Data

(60) Provisional application No. 60/596,151, filed on Sep. 2, 2005, provisional application No. 60/700,948, filed on Jul. 20, 2005.

(51) Int. Cl.
*G01N 33/53* (2006.01)
*G01N 33/567* (2006.01)
*G01N 33/574* (2006.01)
*G01N 33/48* (2006.01)
*G01N 21/00* (2006.01)
*G01N 21/75* (2006.01)
*G01N 33/566* (2006.01)

(52) U.S. Cl. ......... 435/7.92; 435/7; 435/7.1; 435/7.21; 435/7.23; 436/63; 436/64; 436/164; 436/501; 436/503

(58) Field of Classification Search .............. 435/4, 7.1, 435/7.21, 7.23, 7.92; 436/63, 64, 164, 501, 436/503
See application file for complete search history.

(56) References Cited

U.S. PATENT DOCUMENTS

| 5,849,790 | A | 12/1998 | Palmer et al. |
| 6,019,966 | A | 2/2000 | Coleman et al. |
| 6,100,090 | A | 8/2000 | Monia et al. |
| 6,265,160 | B1 | 7/2001 | Leonard |
| 6,426,331 | B1 | 7/2002 | McKinney et al. |
| 7,238,372 | B2 | 7/2007 | Turkson et al. |
| 2004/0175369 | A1 | 9/2004 | Yu et al. |
| 2004/0214166 | A1 | 10/2004 | Li |
| 2004/0248151 | A1 | 12/2004 | Bacus et al. |
| 2005/0080131 | A1 | 4/2005 | Kay et al. |
| 2005/0260646 | A1 | 11/2005 | Baker et al. |
| 2005/0288365 | A1 | 12/2005 | Kay et al. |

FOREIGN PATENT DOCUMENTS

| WO | WO 00/44774 | 8/2000 |
| WO | WO 2005/044091 | 5/2005 |
| WO | WO 2005/110477 | 11/2005 |

OTHER PUBLICATIONS

Dhir et al. Stat3 activation in prostatic carcinomas. The Prostate 51: 241-246, 2002.*
United States Office Action for U.S. Appl. No. 11/300,619 dated Jun. 5, 2008 (11 pages).
Mapara, M.Y. et al., "Tolerance and cancer: mechanisms of tumor evasion and strategies for breaking tolerance," J. Clin. Oncol. (2004) 22(6):1136-1151.
United States Office Action for U.S. Appl. No. 11/300,619 dated Mar. 5, 2009 (10 pages).
European Office Action for Application No. 05778394.6 dated Dec. 18, 2007 (3 pages).
United States Office Action for U.S. Appl. No. 11/102,911 dated Nov. 26, 2008 (14 pages).
Gura, T., "Systems for identifying new drugs are often faulty," Science (1997) 278:1041-1042.
United States Patent Office Action for U.S. Appl. No. 11/300,619 dated Oct. 28, 2009 (14 pages).
United States Patent Office Action for U.S. Appl. No. 11/102,911 dated Mar. 16, 2010 (12 pages).
United States Patent Office Action for U.S. Appl. No. 11/300,619 dated Jun. 9, 2010 (9 pages).
United States Patent Office Action for U.S. Appl. No. 11/581,293 dated Dec. 13, 2010 (13 pages).
Valdembri, D. et al., "In vivo activation of JAK2/STAT-3 pathway during angiogenesis induced by GM-CSF," FASEB J. (2002) 16(2):225-227.
United States Patent Office Notice of Allowance for U.S. Appl. No. 11/300,619 dated Nov. 26, 2010 (5 pages).
Adida C, et al. (1998) "Developmentally regulated expression of the novel cancer anti-apoptosis gene survivin in human and mouse differentiation" *Am J Pathol* 152:43-9.
Akira, S. (2000) "Roles of STAT3 defined by tissue-specific gene targeting." *Oncogene*, 19: 2607-2611. Alas S, Bonavida B. (2001) "Rituximab inactivates signal tranducer and activation of transcription 3 (STAT3) activity in B-non-Hodgkin's lymphoma through inhibition of the interleukin 10 autocrine/paracrine loop and results in down-regulation of Bc1-2 and sensitization to cytotoxic drugs." *Cancer Res* 61:5137-44.
Alas S, Bonavida B. (2003) "Inhibition of constitutive STAT3 activity sensitizes resistant non Hodgkin's lymphoma and multiple myeloma to chemotherapeutic drug-mediated apoptosis." *Clin Cancer Res* 9:316-26.
Altieri DC. (2003) "Survivin and apoptosis control." *Adv Cancer Res* 88:31-52.
Altieri DC. (2003) "Validating Survivin as a cancer therapeutic target." *Nat Rev Cancer* 3:46-54.
Alvarez JV and Frank DA. (2004). "Genome-Wide Analysis of STAT Target Genes" *Cancer Biol Ther*, 3, 1045-50.

(Continued)

*Primary Examiner* — Alana H Dent
(74) *Attorney, Agent, or Firm* — Michael Best & Friedrich LLP

(57) ABSTRACT

Methods are provided for predicting responsiveness of cancer cells to chemotherapy by measuring the level of phosphorylated Stat or the level of expression of Survivin in a cancer and comparing the level in the cancer cell to the respective level in a control. Also provided are methods of selecting a chemotherapeutic treatment for a subject diagnosed with cancer by measuring the level of phosphorylated Stat or the level of expression of Survivin in a cancer and comparing the level in the cancer cell to the respective level in a control. Kits for performing the methods are also provided. Methods for modulating Survivin-dependent apoptosis in a cancer cell are also disclosed.

22 Claims, 9 Drawing Sheets

OTHER PUBLICATIONS

Alvarez, et al. (2006) Signal Transducer and Activator of Transcription 3 Is Required for the Oncogenic Effects of Non-Small-Cell Lung Cancer—Associated Mutations of the Epidermal Growth Factor Receptor *Cancer Research* 66: (6).

Amann J, et al.(2005) "Aberrant epidermal growth factor receptor signaling and enhanced sensitivity to EGFR inhibitors in lung cancer." *Cancer Res* 65:226-35.

Ambrosini G, Adida C, Altieri DC. (1997) "A novel anti-apoptosis gene, survivin, expressed in cancer and lymphoma." *Nat Med* 3:917-21.

Aoki Y, Feldman GM, Tosato G.(2003) "Inhibition of STAT3 signaling induces apoptosis and decreases survivin expression in primary effusion lymphoma." *Blood* 101:1535-42.

Arber, D. A. (2002) "Effect of prolonged formalin fixation on the immunohistochemical reactivity of breast markers." *Appl Immunohistochem Mol Morphol* 10: 183-186.

Archer CD, et al. (2003) "Early changes in apoptosis and proliferation following primary chemotherapy for breast cancer." *Br J Cancer* 89:1035-41.

Ballif BA and Blenis J. (2001)."Molecular Mechanisms Mediating Mammalian Mitogenactivated Protein Kinase (MAPK) Kinase (MEK)-MAPK Cell Survival Signals" *Cell Growth Differ* 12, 397-408.

Bear HD, et al. (2003) "The effect on tumor response of adding sequential preoperative docetaxel to preoperative doxorubicin and cyclophosphamide: preliminary results from National Surgical Adjuvant Breast and Bowel Project Protocol B-27." *J Clin Oncol* 21:4165-74.

Bear HD, et al: (2006) "Sequential preoperative or postoperative docetaxel added to preoperative doxorubicin plus cyclophosphamide for operable breast cancer:National Surgical Adjuvant Breast and Bowel Project Protocol B-27." *J Clin Oncol* 24:2019-27.

Belsches-Jablonski AP, et al: (2001) "Src family kinases and HER2 interactions in human breast cancer cell growth and survival." *Oncogene* 20:1465-75.

Bilous M, et al. (2003) "Predicting the HER2 status of breast cancer from basic histophatology data: an analysis of 1500 breast cancers as part of the HER2000 International Study." *Breast* 12: 92-8.

Biscardi JS, et al: (2000) "Tyrosine kinase signalling in breast cancer: epidermal growth factor receptor and c-Src interactions in breast cancer." *Breast Cancer Res* 2:203-10.

Biscardi JS, Tice DA, Parsons SJ (1999) "c-Src, receptor tyrosine kinases, and human cancer." *Adv Cancer Res* 76:61-119.

Biscardi, J.S., Belsches, A.P. and Parsons, S.J. (1998) "Characterization of human epidermal growth factor receptor and c-Src interactions in human breast tumor cells." *Mol. Carcinog.* 21: 261-272.

Bishop JM. (1998) "The molecular genetics of cancer." *Science* 235:305-11.

Blaskovich Ma, et al. (2003)."Discovery of JSI-124 (Cucurbitacin I), a Selective Janus Kinase/Signal Transducer and Activator of Transcription 3 Signaling Pathway Inhibitor with Potent Antitumor Activity against Human and Murine Cancer Cells in Mice" *Cancer Res* 63, 1270-9.

Bolstad BM, Irizarry RA, Astrand M, Speed TP.(2003) "A comparison of normalization methods for high density oligonucleotide array data based on variance and bias." *Bioinformatics* 19:185-93.

Bonadonna, G., et al. (1998) "Primary chemotherapy in operable breast cancer: eight-year experience at the Milan Cancer Institute." *J Clin Oncol*, 16: 93-100.

Boonyaratanakornkit V, et al. (2001) "Progesterone receptor contains a proline-rich motif that directly interacts wtih SH3 domains and activates c-Src family of tyrosine kinases." *Mol Cell* 8:269-280.

Borg A, et al. "HER-2/neu Amplification Predicts Poor Survival in Node-positive Breast Cancer". (1990). *Cancer Res*, 50, 4332-7.

Bos JL. (1989)."ras Oncogenes in Human Cancer: A Review" *Cancer Res*, 49, 4682-9.

Boschelli, D. H., et al.(2003) "Investigation of the effect of varying the 4-anilino and 7-alkoxy groups of 3-quinolinecarbonitriles on the inhibition of Src kinase activity." *Bioorg Med Chem Lett* 13: 3797-3800.

Bowman, T., et al. (2001) "Stat3-mediated Myc expression is required for Src transformation and PDGF-induced mitogenesis" *Proc Natl Acad Sci USA*, 98: 7319-7324.

Bowman, T., Garcia, R., Turkson, J., and Jove, R. (2000) "STATs in oncogenesis." *Oncogene*, 19: 2474-2488.

Bromberg J, Darnell JE, Jr. (2000) "The role of STATs in transcriptional control and their impact on cellular function." *Oncogene* 19:2468-73.

Bromberg J.(2000) "Signal transducers and activators of transcription as regulators of growth, apoptosis and breast development." *Breast Cancer Res* 2:86-90.

Bromberg JF, (1999) "Wrzeszczynska MH, Devgan G, et al. Stat3 as an oncogene." *Cell* 98:295-303.

Buettner R, Mora LB, Jove R. (2002) "Activated STAT signaling in human tumors provides novel molecular targets for therapeutic intervention." *Clin Cancer Res* 8:945-54.

Cappuzzo F, Hirsch FR, Rossi E, et al. (2005) "Epidermal growth factor receptor gene and protein and gefitinib sensitivity in non-small-cell lung cancer." *J Natl Cancer Inst* 97:643-55.

Cappuzzo F, Varella-Garcia M, Shigematsu H, et al.(2005 "Increased HER2 gene copy number is associated with response to gefitinib therapy in epidermal growth factor receptor-positive non-small-cell lung cancer patients." *J Clin Oncol* 23:5007-18.

Carman CV and Benovic JL. (1998). "G-protein-coupled receptors: turn-ons and turn-offs" *Curr Opin Neurobiol*, 8, 335-44.

Catlett-Falcone R, Dalton WS, Jove R: (1999) "STAT proteins as novel targets for cancer therapy." *Curr Opin Oncol* 11:490-496.

Catlett-Falcone R, Landowski TH, Oshiro MM, et al. (1999) "Constitutive activation of Stat3 signaling confers resistance to apoptosis in human U266 myeloma cells." *Immunity* 10:105-15.

Citron ML, et al: "Randomized trial of dose-dense versus conventionally scheduled and sequential versus concurrent combination chemotherapy as postoperative adjuvant treatment of node-positive primary breast cancer: first report of Intergroup Trial C9741/Cancer and Leukemia Group B Trial 9741". *J Clin Oncol* 21:1431-9, 2003.

Cooper (2006) Phase II study of dose-dense sequential doxorubicin and docetaxel for patients with advanced operable and inoperable breast cancer *Breast Cancer Res Treat* 97: 311-318.

Cooper B, Silverman P, Overmoyer B, et al: (2003) "Dose-dense doxorubicin for patients with advanced operable and inoperable breast cancer [abstract 342]." *Proc Am Soc Clin Oncol* 22:86.

Cortas T, et al. (2005) Activation state (phosphorylated) EGFR and STAT3 as prognostic markers in resected non-small cell lung cancer (NSCLC). In: Proceedings of the American Society of Clinical Oncology, *Abstract #7090*; 2005; Orlando, Florida.

Cox Me, et al. (2000)."Activated 3*,5*-Cyclic AMP-dependent Protein Kinase Is Sufficient to Induce Neuroendocrine-like Differentiation of the LNCaP Prostate Tumor Cell Line*" *J Biol Chem*, 275, 13812-8.

Darnell JE, Jr. (1997) "STATs and gene regulation" *Science* 1997;277:1630-5.

Darnell JE, Jr., Kerr IM, Stark GR: (1994) "Jak-STAT pathways and transcriptional activation in response to IFNs and other extracellular signaling proteins." *Science* 264:1415-21.

Darnell JE. (2002) "Transcription factors as targets for cancer therapy." *Nat Rev Cancer* 2:740-49.

Davis JM, et al: (2003) "Raf-1 and Bcl-2 induce distinct and common pathways that contribute to breast cancer drug resistance." *Clin Cancer Res* 9:1161-70.

Dearmond D, et al. (2003) "Autocrine-mediated ErbB-2 kinase activation of STAT3 is required for growth factor independence of pancreatic cancer cell lines." *Oncogene* 22:7781-95.

Dhillon AS and Kolch W. (2002). "Untying the regulation of the Raf-1 kinase" *Arch Biochem Biophys*, 404, 3-9.

Di Marco E, et al.(1989) "Autocrine interaction between TGF alpha and the EGF-receptor: quantitative requirements for induction of the malignant phenotype." *Oncogene*, 4, 831-8.

Diaz N, Minton S, Cox C, et al: (2006) "Activation of stat3 in primary tumors from high-risk breast cancer patients is associated with elevated levels of activated SRC and survivin expression." *Clin Cancer Res* 12:20-8.

Dolled-Filhart M, et al. (2003) "Tissue microarray analysis of signal transducers and activators of transcription 3 (Stat3) and phospho- Stat3 (Tyr705) in node-negative breast cancer shows nuclear localization is associated with a better prognosis." *Clin Cancer Res* 9:594-600.

Dumaz N and Marais R. (2005). "Integrating signals between cAMP and the RAS/RAF/MEK/ERK signalling pathways" *Febs J*, 272, 3491-504.

English JM and Cobb MH. (2002). "Pharmacological inhibitors of MAPK pathways" *Trends Pharmacol Sci*, 23, 40-5.

Enserink JM, et al. (2002). "A novel Epac-specific cAMP analogue demonstrates independent regulation of Rap1 and ERK" *Nat Cell Biol*, 4, 901-6.

Epling-Burnette PK, et al.(2001) "Inhibition of STAT3 signaling leads to apoptosis of leukemic large granular lymphocytes and decreased Mcl-1 expression." *J Clin Invest* 107:351-62.

Epling-Burnette, PK, et al. (2001) "Cooperative regulation of Mcl-1 by Janus kinase/stat and phosphatidylinositol 3-kinase contribute to granulocyte-macrophage colony-stimulating factor-delayed apoptosis in human neutrophils." *J Immunol*, 166: 7486-7495.

Erhardt P, et al. (1995). "Differential Regulation of Raf-1 and B-Raf and Ras-Dependent Activation of Mitogen-Activated Protein Kinase by Cyclic AMP in PC12 Cells" *Mol Cell Biol*, 15, 5524-30.

Ezzat AA, Rahal M, Ajarim D, et al: (2003) "Dose dense neoadjuvant sequential chemotherapy in the management of locally advanced breast cancer: A phase II study [Abstract 202]." *Proc Am Soc Clin Oncol* 22:51, 2003.

Fernandes A, Hamburger AW, Gerwin BI. (1999) "ErbB-2 kinase is required for constitutive stat 3 activation in malignant human lung epithelial cells." *Int J Cancer* 83:564-70.

Fleming TP, Matsui T and Aaronson SA. (1992). "Platelet-derived growth factor (PDGF) receptor activation if cell transformation and human malignancy" *Exp Gerontol*, 27, 523-32.

Fresno Vara JA, et al. (2004). "PI3K/Akt signalling pathway and cancer" *Cancer Treat Rev*, 30, 193-204.

Fujishita T, Loda M, Turner RE, et al.(2003) "Sensitivity of non-small-cell lung cancer cell lines established from patients treated with prolonged infusions of Paclitaxel." *Oncology* 64:399-406.

Garcia R, et al: (2001) "Constitutive activation of Stat3 by the Src and JAK tyrosine kinases participates in growth regulation of human breast carcinoma cells." *Oncogene* 20:2499-513.

Garcia R, et al: Constitutive activation of Stat3 in fibroblasts transformed by diverse oncoproteins and in breast carcinoma cells. Cell Growth Differ 8:1267-76, 1997.

Gergely, F., et al. (2000) "The TACC domain identifies a family of centrosornal proteins that can interact with microtubules." *Proc Natl Acad Sci USA*, 97: 14352-14357.

Ghafoor, A., Samuels, A., and Jemal, A. (2003) Breast cancer facts and figures 2003-2004.) *American Cancer Society*.

Giaccone G, et al. (2004) "Gefitinib in combination with gemcitabine and cisplatin in advanced non-small-cell lung cancer: a phase III trial—INTACT 1." *J Clin Oncol* 22:777-84.

Graells J, et al. (2004) "Overproduction of VEGF165 Concomitantly Expressed with its Receptors Promotes Growth and Survival of Melanoma Cells through MAPK and PI3K Signaling" *J Invest Dermatol*, 123, 1151-61.

Grandis JR, et al. (1998) "Requirement of Stat3 but not Stat1 activation for epidermal growth factor receptor-mediated cell growth in vitro." *J Clin Invest* 102:1385-92.

Grandis JR, et al.(2000) "Constitutive activation of Stat3 signaling abrogates apoptosis in squamous cell carcinogenesis in vivo." *Proc Natl Acad Sci U S A* 97:4227-32.

Grassi V, et al. (1986). "Oral beta 2-selective adrenergic bronchodilators" *Int J Clin Pharmacol Res*, 6, 93-103.

Graves LM, et al. (1993)."Protein kinase A antagonizes platelet-derived growth factor-induced signaling by mitogen-activated protein kinase in human arterial smooth muscle cells" *Proc Natl Acad Sci U S A*, 90, 10300-4.

Gritsko T, et al: (2006) "PerSistent activation of stat3 signaling induces survivin gene expression and confers resistance to apoptosis in human breast cancer cells." *Clin Cancer Res* 12:11-9.

Hafner S, et al. (1994) "Mechanism of Inhibition of Raf-1 by Protein Kinase A" *Mol Cell Biol*, 14, 6696-703.

Hagemann C and Blank JL. (2001). "The ups and downs of MEK kinase interactions" *Cell Signal*, 13, 863-75.

Hahn WC, Weinberg RA. (2002) "Modelling the molecular circuitry of cancer." *Nat Rev Cancer* 2:331-41.

Hanahan D and Weinberg RA. (2000). "The Hallmarks of Cancer" *Cell*, 100, 57-70.

Hao D and Rowinsky EK. (2002). "Inhibiting Signal Transduction: Recent Advances in the Development of Receptor Tyrosine Kinase and Ras Inhibitors" *Cancer Invest*, 20, 387-404.

Hattori M, Sakamoto H, Satoh K, Yamamoto T. DN (2001) "A demethylase is expressed in ovarian cancers and the expression correlates with demethylation of CpG sites in the promoter region of c-erbB-2 and survivin genes." *Cancer Lett* 169:155-64.

Haura, et al. (2005) Activated Epidermal Growth Factor Receptor ^Stat-3 Signaling Promotes Tumor Survival in vivo in Non ^Small Cell Lung Cancer *Clin Cancer Res* 11(23) 8288.

Hayes, D. F. and Thor, A D. (2002) c-erbB2 in breast cancer: development of a clinically useful marker. *Semin Oncol*, 29: 231-245,.

Herbst RS, Fukuoka M, Baselga J. (2004) "Gefitinib—a novel targeted approach to treating cancer." *Nat Rev Cancer* 4:956-65.

Herbst RS, Giaccone G, Schiller JH, et al.(2004) "Gefitinib in combination with paclitaxel and carboplatin in advanced non-small-cell lung cancer: a phase III trial—INTACT 2." *J Clin Oncol* 22:785-94.

Herbst RS, Prager D, Hermann R, et al. (2005) "TRIBUTE: A Phase III Trial of Erlotinib Hydrochloride (OSI-774) Combined With Carboplatin and Paclitaxel Chemotherapy in Advanced Non-Small-Cell Lung Cancer." 23:5892-9.

Hildesheim, J. and Fornace Jr., A. J. (2002) "Gadd45a: an elusive yet attractive candidate gene in pancreatic cancer." *Clin Cancer Res*, 8: 2475-2479 [Comment on: Clin Cancer Res, 2002. 8:2563-2569].

Hirano, T., Ishihara, K, and Hibi, M. (2000) "Roles of STAT3 in mediating the cell growth. Differentiation and survival signals relayed through the IL-6 family of cytokine receptors." *Oncogene*, 19: 2548-2556.

Hirsch FR, et al. (2005) "Increased Epidermal Growth Factor Receptor Gene Copy Number Detected by Fluorescence In Situ Hybridization Associates With Increased Sensitivity to Gefitinib in Patients With Bronchioloalveolar Carcinoma Subtypes: A Southwest Oncology Group Study" *J Clin Oncol* Jul. 5, 2005; [Epub ahead of print].

Hoffman WH, et al. (2002)"Transcriptional repression of the anti-apoptotic survivin gene by wild type p53." *J Biol Chem* 277:3247-57.

Hudis C, et al: (1999) "Sequential dose-dense doxorubicin, paclitaxel, and cyclophosphamide for resectable high-risk breast cancer: feasibility and efficacy." *J Clin Oncol* 17:93-100.

Hung W, Elliott, B. (2001) "Co-operative effect of c-Src tyrosine kinase and Stat3 in activation of hepatocyte growth factor expression in mammary carcinoma cells." *J Biol Chem* 276:12395-403.

Irizarry RA, et al., (2003) Speed TP. Exploration, normalization, and summaries of high density oligonucleotide array probe level data *Biostatistics* 4:249-64.

Irizarry, RA, et al. (2003) "Summaries of Affymetrix GeneChip probe level data." *Nucleic Acids Res*, 31: e15, 2003.

Islam A, et al. (2000) "High expression of Survivin, mapped to 17q25, is significantly associated with poor prognostic factors and promotes cell survival in human neuroblastoma". *Oncogene* 19:617-23.

Jiang Z, et al. (2004). "Alpha-methylacyl-CoA racemase: a multi-institutional study of a new prostate cancer marker" *Histopathology*, 45, 218-25.

Jin W, et al. (2003). "Roles of the PI-3K and MEK pathways in Ras-mediated chemoresistance in breast cancer cells" *Br J Cancer*, 89, 185-91.

Johnson GL and Lapadat R. (2002) "Mitogen-Activated Protein Kinase Pathways by ERK, JNK and p38 Protein Kinases." *Science*, 298, 1911-2.

Johnson JR, et al. (2005). "Approval Summary for Erlotinib for Treatment of Patients with LocallyAdvanced orMetastatic Non ₐSmall Cell Lung Cancer after Failure of at Least One Prior Chemotherapy Regimen" *Clin Cancer Res*, 11, 6414-21.

Kanda N, et al. (2004) "STAT3 is constitutively activated and supports cell survival in association with survivin expression in gastric cancer cells." *Oncogene* 23:4921-9.

Kaplan DH, et al. (1998) "Demonstration of an interferon γ-dependent tumor surveillance system in immunocompetent mice." *Proc Natl Acad Sci USA* 95:7556-61.

Karni R, Jove R, Levitzki A. (1999) "Inhibition of pp60c-Src reduces Bcl-XL expression and reverses the transformed phenotype of cells overexpressing EGF and HER-2 receptors." *Oncogene* 18:4654-62.

Karras JG, et al.(2000) "STAT3 regulates the growth and immunoglobulin production of BCL (1) B cell lymphoma through control of cell cycle progression." *Cell Immunol* 202:124-35.

Khosravi-Far R, et al. (1996)."Oncogenic Ras Activation of Raf/Mitogen-Activated Protein Kinase-Independent Pathways Is Sufficient to Cause Tumorigenic Transformation" *Mol Cell Biol*, 16, 3923-33.

Kimura, Y., et al.. (1997) "Cdc37 is a molecular chaperone with specific functions in signal transduction" *Genes Dev*, 11: 1775-1785.

Kloth MT, et al..(2003) "STAT5b, a mediator of synergism between c-Src and the epidermal growth factor receptor." *J Biol Chem* 278:1671-9.

Kobayashi, K., et al. (1999) "Expression of a murine homologue of the inhibitor of apoptosis protein is related to cell proliferation." *Proc Natl Acad Sci USA*, 96: 1457-1462.

Kris MG, Natale RB, Herbst RS, et al. (2003) "Efficacy of gefitinib, an inhibitor of the epidermal growth factor receptor tyrosine kinase, in symptomatic patients with non-small cell lung cancer: a randomized trial." *Jama* 290:2149-58.

Kuerer HM, et al: (1999) "Clinical course of breast cancer patients with complete pathologic primary tumor and axillary lymph node response to doxorubicin-based neoadjuvant chemotherapy." *J Clin Oncol* 17:460-9.

Lerner EC, et al. (1997). "Inhibition of the prenylation of K-Ras, but not H- or N-Ras, is highly resistant to CAAX peptidomimetics and requires both a farnesyltransferase and a geranylgeranyltransferase I inhibitor in human tumor cell lines" *Oncogene*, 15, 1283-8.

Levy DE, Darnell JE. (2002) "STATs: transcriptional control and biologic impact." *Nat Rev Mol Cell Biol* 2002;3:651-62.

Li F, Altieri DC. (1999) "Transcriptional analysis of human survivin gene expression." *Biochem J* 344:305-11.

Li L, Shaw PE: (2002) "Autocrine-mediated activation of STAT3 correlates with cell proliferation in breast carcinoma lines." *J Biol Chem* 277:17397-405.

Li X, et al. (1995) "Single step procedure for labeling DNA strand breaks with fluorescein- or BODIPY-conjugated deoxynucleotides: detection of apoptosis and bromodeoxyuridine incorporation." *Cytometry* 20:172-180.

Lin TS, Mahajan S, Frank DA. (2000) "STAT signaling in the pathogenesis and treatment of leukemias." *Oncogene* 19:2496-2504.

Lynch TJ, Bell DW, Sordella R, et al. (2004) "Activating mutations in the epidermal growth factor receptor underlying responsiveness of non-small-cell lung cancer to gefitinib." *N. Engl J Med* 350:2129-39.

MacDonald, D. H., et al. (1999) "Cloning and characterization of RNF6, a novel RING finger gene mapping to 13q12." *Genomics*, 58: 94-97.

Mahboubi K, et al. (2001) "Interleukin-11 up-regulates survivin expression in endothelial cells through a signal transducer and activator of transcription-3 pathway." *Lab Invest* 81:327-34.

Maudsley S, et al. (2000) "The b2-Adrenergic Receptor Mediates Extracellular Signal-regulated Kinase Activation via Assembly of a Multi-receptor Complex with the Epidermal Growth Factor Receptor*" *J Biol Chem* 275(13), 9572-9580.

McCready DR, et al: (1989) "The prognostic significance of lymph node metastases after preoperative chemotherapy for locally advanced breast cancer." *Arch Surg* 124:21-5.

Miller KD, et al: (1999) "Combination versus sequential doxorubicin and docetaxel as primary chemotherapy for breast cancer: A randomized pilot trial of the Hoosier Oncology Group." *J Clin Oncol* 17:3033-7.

Miller VA, et al. "Bronchioloalveolar pathologic subtype and smoking history predict sensitivity to gefitinib in advanced non-small-cell lung cancer." *J Clin Oncol* 22:1103-9, 2004.

Minna JD, Dowell J. (2005) "Erlotinib hydrochloride." *Nat Rev Drug Discov* Suppl:S14-5.

Mirza A, et al. (2002) "Human survivin is negatively regulated by wild-type p53 and participates in p53-dependent apoptotic pathway." *Oncogene* 21:2613-22.

Moasser MM, Srethapakdi M, Sachar KS, et al: (1999) "Inhibition of Src kinases by a selective tyrosine kinase inhibitor causes mitotic arrest." *Cancer Res* 59:6145-52.

Moore PF, Constantine JW and Barth WE. (1978). "Pirbuterol, a Selective Beta2 Adrenergic Bronchodilator" *J Pharmacol Exp Ther*, 207, 410-8.

Mora LB, et al. (2002) "Constitutive activation of Stat3 in human prostate tumors and cell lines: direct inhibition of Stat3 signaling induces apoptosis of prostate cancer cells." *Cancer Res* 62:6659-66.

Morrell LE, et al: (1998) "A Phase II trial of neoadjuvant methotrexate, vinblastine, doxorubicin, and cisplatin in the treatment of patients with locally advanced breast carcinoma." *Cancer* 82:503-11.

Muchmore, S. W., et al. (2000) "Crystal structure and mutagenic analysis of the inhibitor-of-apoptosis protein survivin." *Mol Cell*, 6: 173-182.

Niu G, et al: (2002) "Roles of activated Src and Stat3 signaling in melanoma tumor cell growth." *Oncogene* 21:7001-10.

Niu, G., et al (2002) "Constitutive Stat3 activity up-regulates VEGF expression and tumor angiogenesis." *Oncogene*, 21: 2000-2008.

O'Connor DS, et. (2002) "A p34(cdc2) survival checkpoint in cancer." *Cancer Cell* 2:43-54.

Oude Weernink, P. A, et al. (1994) "Functional interaction between the epidermal growth factor receptor and c-Src kinase activity." *FEBS Lett*, 352: 296-300.

Paez JG, et al. (2004) "EGFR mutations in lung cancer: correlation with clinical response to gefitinib therapy." *Science* 304:1497-500.

Pao W, et al. (2004) "EGF receptor gene mutations are common in lung cancers from "never smokers" and are associated with sensitivity of tumors to gefitinib and erlotinib." *Proc Natl Acad Sci U S A* ;101: (36) 13306-11.

Pao W, Miller VA. (2005) "Epidermal Growth Factor Receptor Mutations, Small-Molecule Kinase Inhibitors, and Non-Small-Cell Lung Cancer: Current Knowledge and Future Directions". *J Clin Oncol* 23:2556-68.

Pegram MD, Pauletti G, Slamon DJ. (1998) "HER2/neu as a predictive marker of response to breast cancer therapy". *Breast Cancer Res Treat* 52:65-77.

Perez-Soler R, et al. (2004) "Determinants of tumor response and survival with erlotinib in patients with non—small-cell lung cancer." *J Clin Oncol* 22:3238-47.

Pollet, J., et al. (2002) "Overexpression of the myeloma-associated oncogene fibroblast growth factor receptor 3 confers dexamethasone resistance." *Blood*, 100: 3819-3821.

Prenzel N, et al. (2000) "Tyrosine kinase signaling in breast cancer. Epidermal growth factor receptor: convergence point for signal integration and diversification." *Breast Cancer Res* 2:184-190.

Puthier, D., Bataille, R., and Amiot, M. (1999) "IL-6 up-regulates mcl-1 in human myeloma cells through JAK/STAT rather than ras/MAP kinase pathway." *Eur J Immunol*. 29: 3945-3950.

Rahimi, N., et al. (1998) "c-Src kinase activity is required for hepatocyte growth factor-induced motility and anchorage-independent growth of mammary carcinoma cells." *J Biol Chem*, 273: 33714-33721.

Real PJ, et al. (2002) "Resistance to chemotherapy via Stat3-dependent overexpression of Bcl-2 in metastatic breast cancer cells." *Oncogene* 21:7611-18.

Redell MS and Tweardy DJ. (2005)."Targeting Transcription Factors for Cancer Therapy" *Curr Pharm Des*, 11, 2873-87.

Reed, J. C. (2001) "The Survivin saga goes in vivo." J Clin Invest, 108: 965-969.

Ren Z, Schaefer TS. (2002) "ErbB-2 activates Stat3 alpha in a Src and JAK2-dependent manner." *J Biol Chem* 277:38486-93.

Rogers PM, et al:(2002) "Overexpression of BclXL in a human ovarian carcinoma cell line: paradoxic effects on chemosensitivity in vitro versus in vivo." *Int J Cancer* 97:858-63.

Rosen N, et al. (1986) "Analysis of pp60c-src protein kinase activity in human tumor cell lines and tissues." *J Biol Chem* 261:(29) 13754-9.

Ruff-Jamison S, et al. (1994) "Epidermal growth factor and lipopolysaccharide activate Stat3 transcription factor in mouse liver." *J Biol Chem* 269:21933-5.

Sartor CI, et al: Role of epidermal growth factor receptor and STAT-3 activation in autonomous proliferation of SUM-102PT human breast cancer cells. Cancer Res 57:978-87, 1997.
Schmitt JM and Stork PJ. (2001). "Cyclic AMP-Mediated Inhibition of Cell rowth Requires the Small G Protein Rap1" *Mol Cell Biol*, 21, 3671-83.
Schmitt JM and Stork PJ. (2002). "PKA Phosphorylation of Src Mediates cAMP's Inhibition of Cell Growth via Rap1" *Mol Cell*, 9, 85-94.
Schwartz GF, et al: (1994) "Induction chemotherapy followed by breast conservation for locally advanced carcinoma of the breast." *Cancer* 73:362-9.
Sebolt-Leopold JS, et al (1999). "Blockade of the MAP kinase pathway suppresses growth of colon tumors in vivo" *Nat Med*, 5, 810-6.
Sebolt-Leopold JS. (2000). "Development of anticancer drugs targeting the MAP kinase pathway" *Oncogene*, 19, 6594-9.
Secrist, J. P., Zhou, X., and Richon, V. M. (2003) "HDAC inhibitors for the treatment of cancer" *Curr Opin Investig Drugs*, 4; 1422-1427.
Seidel HM, et al. (1995) "Spacing of palindromic half sites as a determinant of selective STAT (signal transducers and activators of transcription) DNA binding and transcriptional activity." *Proc Natl Acad Sci U S A* 92:3041-5.
Sequist LV, Haber DA, Lynch TJ. (2005) "Epidermal growth factor receptor mutations in non-small cell lung cancer: predicting clinical response to kinase inhibitors." *Clin Cancer Res* 11:5668-70.
Sevetson BR, Kong X and Lawrence JC, Jr. (1993). "Increasing cAMP attenuates activation of mitogen-activated protein kinase" *Proc Natl Acad Sci U S A*, 90, 10305-9.
Shah, N. P., et al. (2004) "Overriding imatinib resistance with a novel ABL kinase inhibitor." *Science*, 305: 399-401.
Shen Y, et al. (2001) "Constitutively activated Stat3 protects fibroblasts from serum withdrawal and UV-induced apoptosis and antagonizes the proapoptotic effects of activated Stat1." *Proc Natl Acad Sci U S A* 98:1543-8.
Shepherd FA, P J, et al (2004) "A randomized placebo-controlled trial of erlotinib in patient with advanced non-small cell lung caner (NSSCLC) following failure of 1 st line or 2nd line chemotherapy." *Proc Am Soc Clin Oncol*, 22.
Shepherd FA, et al. (2005) "Erlotinib in previously treated non-small-cell lung cancer." *N Engl J Med* 353:123-32.
Shigematsu H, et al. (2005) "Clinical and biological features associated with epidermal growth factor receptor gene mutations in lung cancers." *J Natl Cancer Inst* 97:339-46.
Sinibaldi, D., (2000). "Induction of p21WAF1/CIP1 and Cyclin DI expression by the Src oncoprotein in mouse flbroblasts: role of activated STAT3 signaling." *Oncogene*, 19: 5419-5427.
Siziopikou KP, et al. (1996) "bcl-2 expression in the spectrum of preinvasive breast lesions." *Cancer* 77:499-506.
Sjostrom J, et al. (2002) "The predictive value of bcl-2, bax, bcl-xL, bag-1, fas, and fasL for chemotherapy response in advanced brest cancer." *Clin Cancer Res* 8:811-6.
Slamon DJ, et al. (1987). "Human Breast Cancer: Correlation of Relapse and Survival with Amplification of the HER-2/neu Oncogene" *Science*, 235, 177-82.
Smith IC, et al: (2002) "Neoadjuvant chemotherapy in breast cancer: significantly enhanced response with docetaxel" *J Clin Oncol* 20:1456-66.
Smith, P. D. and Crompton, M. R. (1998) "Expression of v-src in mammary epithelial cells induces transcription via STAT3." *Biochem J*, 331: 381-385.
Song JI, Grandis JR. (2000) "STAT signaling in head and neck cancer." *Oncogene* 19:2489-95.
Song L, Turkson J, Karras JG, Jove R, Haura EB. (2003) "Activation of Stat3 by receptor tyrosine kinases and cytokines regulates survival in human non-small cell carcinoma cells." *Oncogene* 22:4150-65.
Song Z, Yao X, Wu M. (2003) "Direct interaction between survivin and Smac/DIABLO is essential for the anti-apoptotic activity of survivin during taxol-induced apoptosis." *J Biol Chem* 278:23130-40.
Sordella R, Bell DW, Haber DA, Settleman J. (2004) "Gefitinib-sensitizing EGFR mutations in lung cancer activate anti-apoptotic pathways." *Science* 305:1163-7.

Stearns V, et al: (2003) "A prospective randomized pilot study to evaluate predictors of response in serial core biopsies to single agent neoadjuvant doxorubicin or paclitaxel for patients with locally advanced breast cancer." *Clin Cancer Res* 9:124-33.
Steen SN, Ziment I and Thomas JS. (1974). "Pyrbuterol: A new bronchodilator. Phase 1—Single dose study" *Curr Ther Res Clin Exp*, 16, 1077-81.
Steinberg SF. (2000). "The Cellular Actions of b-Adrenergic Receptor Agonists Looking Beyond cAMP" *Circ Res*, 87, 1079-82.
Still, IH, et al. (1999) "The third member of the transforming acidic coiled coil-containing gene family, TACC3, maps in 4p16, close to translocation breakpoints in multiple myeloma, and is upregulated in various cancer cell lines" *Genomics* 58: 165-170.
Stork PJ and Schmitt JM. (2002) "Crosstalk between cAMP and MAP kinase signaling in the regulation of cell proliferation" *Trends Cell Biol*, 12, 258-66.
Strobl JS, Wonderlin WF and Flynn DC. (1995). "Mitogenic Signal Transduction in Human Breast Cancer Cells" *Gen Pharmacol*, 26, 1643-9.
Sumantran VN, et al: (1995) "Overexpression of Bcl-XS sensitizes MCF-7 cells to chemotherapy-induced apoptosis." *Cancer Res* 55:2507-10.
Sun J, et al.(2003). "Geranylgeranyltransferase I Inhibitor GGTI-2154 Induces Breast Carcinoma Apoptosis and Tumor Regression in H-Ras Transgenic Mice" *Cancer Res*, 63, 8922-9.
Sun J, et al. (2005)."Inhibiting angiogenesis and tumorigenesis by a synthetic molecule that blocks binding of both VEGF and PDGF to their receptors" *Oncogene*, 24, 4701-9.
Tanaka K, et al (2000) "Expression of survivin and its relationship to loss of apoptosis in breast carcinomas." *Clin Cancer Res* 6:127-34.
Tommerup, N. and Vissing, H. (1995) "Isolation and fine mapping of 16 novel human zinc finger-encoding cDNAs identify putative candidate genes for developmental and malignant disorders." *Genomics*, 27: 259-264.
Tortora G and Ciardiello F. (2002). "Protein Kinase A as Target for Novel Integrated Strategies of Cancer Therapy" *Ann N Y Acad Sci*, 968, 139-47.
Touboul E, et al: (1992) "Multidisciplinary treatment approach to locally advanced non-inflammatory breast cancer using chemotherapy and radiotherapy with or without surgery." *Radiother Oncol* 25:167-75.
Tracy S, et al. (2004) "Gefitinib induces apoptosis in the EGFRL858R non-small-cell lung cancer cell line H3255." *Cancer Res* 64:7241-4.
Troadec JD, et al (2002)."Activation of the Mitogen-Activated Protein Kinase (ERK1/2) Signaling Pathway by Cyclic AMP Potentiates the Neuroprotective Effect of the eurotransmitter Noradrenaline on Dopaminergic Neurons" *Mol Pharmacol*, 62, 1043.
Tsao MS, et al. (2005) "Erlotinib in lung cancer—molecular and clinical predictors of outcome." *N Engl J Med* 353:133-44.
Tu Y, et al: (1998) "BCL-X expression in multiple myeloma: possible indicator of chemoresistance." *Cancer Res* 58:256-62.
Turkson J, et al. (1998) "Stat3 activation by Src induces specific gene regulation and is required for cell transformation." *Mol Cell Biol* 18:2545-52.
Turkson J, Jove R. (2000) "STAT proteins: novel molecular targets for cancer drug discovery." *Oncogene* 19:6613-26.
Turkson J, et al: (2004) "Novel peptidomimetic inhibitors of signal transducer and activator of transcription 3 dimerization and biological activity." *Mol Cancer Ther* 3:261-9.
Turkson J, et al. (2001) "Phosphotyrosyl peptides block Stat3-mediated DNA-binding activity, gene regulation and cell transformation." *J Biol Chem* 276:45443-55.
Turkson J, et al. (2004) "Inhibition of constitutive signal transducer and activator of transcription 3 activation by novel platinum complexes with potent antitumor activity." *Mol Cancer Ther* 3:1533-42.
Turkson J. (2004) "STAT proteins as novel targets for cancer drug discovery." *Expert Opin Ther Targets* 8:409-22.
Tusher VG, et al. (2001) "Significance analysis of miccroarrays applied to the ionizing radiation response." *Proc Natl Acad Sci USA* 98:5116-21.

Van Gelder RN, et al. (1990) "Amplified RNA synthesized from limited quantities of heterogeneous cDNA." *Proc Natl Acad Sci USA* 87:1663-7.

Von Minckwitz G, et al: (2001) "Dose-dense doxorubicin, docetaxel, and granulocyte colony-stimulating factor support with or without tamoxifen as preoperative therapy in patients with operable carcinoma of the breast: a randomized, controlled, open phase IIb study." *J Clin Oncol* 19:3506-15.

Vossler MR, et al. (1997) "cAMP Activates MAP Kinase and Elk-1 through a B-Raf- and Rap1-Dependent Pathway" *Cell*, 89, 73-82.

Wade, P. A. and Wolffe, A. P. (1999) "Transcriptional regulation: Switching circuitry." *Curr Biol*, 9: R221-R224.

Wang L, Zhang GM, Feng ZH: (2003) "Down-regulation of survivin expression reversed multidrug resistance in adriamycin-resistant HL-60/ADR cell line." *Acta Pharmacol Sin* 24:1235-40.

Warrington, JA, et al.(2000) "Comparison of human adult and fetal expression and identification of 535 housekeeping/maintenance genes." *Physiol Genomics*, 2: 143-147.

Watanabe M, et al. (1996) "An effect of K-ras gene mutation on epidermal growth factor receptor signal transduction in PANC-1 pancreatic carcinoma cells." *Int J Cancer*, 67, 264-8.

Watson CJ, Miller WR.(1995) "Elevated levels of members of the STAT family of transcription factors in breast carcinoma nuclear extracts." *Br J Cancer* 71: 840-4.

Weinstein, I. B. (2002) "Cancer. Addiction to Oncogenes—the Achilles heal of cancer." *Science*, 297: 63-64.

Weinstein-Oppenheimer CR, et al. (2000) "The Raf signal transduction cascade as a target for chemotherapeutic intervention in growth factor-responsive tumors" *Pharmacol Ther*, 88, 229-79.

Weldon CB, et al. (2002) "Idenetification of mitogen-activatedprotein kinase kinase as a chemoresistant pathway in MCF-7 cells by using gene expression microarray" *Surgery*, 132, 293-301.

Wells J, et al. (2000) "Target gene specificity of E2F and pocket protein family members in living cells." *Mol Cell Biol* 20:5797-807.

Widschwendter A., et al. (2002) "Prognostic significance of signal transducer and activator of transcription 1 activation in breast cancer." *Clin Cancer Res* 8:3065-74.

Wojcik, et al. (2006) A novel activating function of c-Src and Stat3 on HGF transcription in mammary carcinoma cells *Oncogene* 25, 2773-2784.

Wolmark N, et al: (2001) "Preoperative chemotherapy in patients with operable breast cancer: nine-year results from National Surgical Adjuvant Breast and Bowel Project B-18." *J Natl Cancer Inst Monogr*: 96-102, 2001.

Wu J, et al. (1993) "Inhibition of the EGF-Activated MAP Kinase Signaling Pathway by Adenosine 3#,5#-Monophosphate" *Science*, 262, 1065-9.

Xi S, et al. (2003) "Src kinases mediate STAT growth pathways in squamous cell carcinoma of the head and neck." *J Biol Chem* 278:31574-83.

Yamamoto, et al. (2000) "Cross-talk between signal transducer and activator of transcription 3 and estrogen receptor signaling." *FEBS Lett* 486:143-8.

Yu CL,et al. (1995) "Enhanced DNA-binding activity of a Stat3-related protein in cells transformed by the Src oncoprotein." *Science* 269:81-3.

Yu H, Jove R. (2004) "The STATs of cancer—new molecular targets come of age." *Nat Rev Cancer* 4: 97-105.

Zaffaroni N, et al: (2002) "Expression of the anti-apoptotic gene surviving correlates with taxol resistance in human ovarian cancer." *Cell Mol Life Sci* 59:1406-12.

Zhang Y, et al. (2000) "Activation of Stat3 in v-Src-transformed fibroblasts requires cooperation of Jak1 kinase activity." *J Biol Chem* 275:24935-44.

Zhang, F., et al. (2003) "Delineating an oncostatin M-activated STAT3 signaling pathway that coordinates the expression of genes involved in cell cycle regulation and extarcellular matrix deposition of MCF-7 cells." *Oncogene*, 22: 894-905.

Zhang, J. H., Zhang, Y., and Herman, B. (2003) "Caspases, apoptosis and aging." *Ageing Res Rev*, 2: 357-366.

Zheng Z, Bepler G, Cantor A, Haura EB.(2005) "Small tumor size and limited smoking history predicts activated epidermal growth factor receptor in early-stage non-small cell lung cancer." *Chest* 128:308-16.

Zhong, Z., Wen, Z., and Darnell, J. E., Jr.(1994) "Stat3: a STAT family member activated by tyrosine phosphorylation in response to epidermal growth factor and interleukin-6." *Science*, 264: 95-98.

Zhou, M., et al. (2002) "DNA damage induces a novel p53-survivin signaling pathway regulating cell cycle and apoptosis in acute lymphoblastic leukemia cells." *J Pharmacol Exp Ther*, 303: 124-131.

United States Patent Office Action for U.S. Appl. No. 11/102,911 dated Jul. 22, 2009 (15 pages).

U.S. Appl. No. 11/581,293, filed Oct. 16, 2006, Torres-Roca.

Ardizzoni, A. et al., "The combination of etoposide and cisplatin in non-small-cell lung cancer (NSCLC)," Ann. Oncal. (1999) 10:S13-17.

Bartoli, M. et al., "VEGF differentially activates Stat3 in microvascular endothelial cells," FASEB J. (2003) 17:1562-1564.

Bromberg, J.F. et al., "Transcriptionally active Stat1 is requited for the antiproliferative effects of both interferon alpha and interferon gamma," Proc. Natl. Acad. Sci. (1996) 93:7673-7678.

Bromberg, J.F. et al., "Stat3 activation is required for cellular transformation by v-src," Mol. Cell Biol. (1998) 18:2553-2558.

Calvin, D.P. et al., "Inhibition of Stat3 activity with Stat3 antisense oligonucleotide (Stat3-ASO) enhances radiation-induced apoptosis in DU145 prostate cancer cells," Int. J. Radiat. Oncol. Biol. Phys. (2003) 57:S297 Proceedings of the 45th Annual ASTRO Meeting.

Fukada, T. et al., "Two signals are necessary for cell proliferation induced by a cytokine receptor gp130: involvement of STAT3 in anti-apoptosis," Immunity (1996) 5:449-460.

Garcia, R. et al., "Activation of STAT transcription factors in oncogeqic tyrosine kinase signaling," J. Biomed. Sci. (1998) 5:79-85.

Gouilleux, F. et al., "Prolactin and interleukin-2 receptors in T lymphocytes signal through a MGF-STATS-like transcription factor," Endocrinology (1995) 136:5700-5708.

Grandis, R.J. et al., "Epidermal growth factor receptor-mediated stat3 signaling blocks apoptosis in head and neck cancer," Laryngoscope (2000b) 110:868-874.

Horiguchi, A. et al., "STAT3, but not ERKs mediates the IL6-induced prolifeation of renal cancer cells, ACHN and 769P," Kidney Int. (2002) 61:926-938.

Hung, W. et al., "Co-operative effect of c-Src tyrosine kinase and Stat3 in activation of hepatocyte growth factor expression in mammary carcinoma cells," J. Biol. Chem. (2001) 276(15):12395-12403.

Jing, N. et al., "G-quartet oligonucleotides: a new class of signal transducer and activator of transcription 3 inhibitors that suppresses growth of prostate and breast tumors through induction of apoptosis," Cancer Res. (2004) 64:6603-6609.

Klement, G. et al., "Continuous low-dose therapy with vinblastine and VEGF receptor-2 antibody induces sustained tumor regression without overt toxicity," J. Clin. Invest. (2000) 105:R15-24.

Klement, G. et al., "Differences in therapeutic indexes of combination metronomic chemotherapy and an anti-VEGFR-2 antibody in multidrug-resistant human breast cancer xenografts," Clin. Cancer Res. (2002) 8:221-232.

Kotenko, S.V. et al., "Jak-Stat signal transduction pathway through the eyes of cytokine class II receptor complexes," Oncogene (2000) 19:2557-2565.

Nielsen, M. et al., "Constitutive activation of a slowly migrating isoform of Stat3 in mycosis fungoides: tryphostin AG490 inhibits Stat3 activation and growth of mycosis fungoides tumor cell lines," Pro. Natl. Acad. Sci. USA (1997) 94:6764-6769.

Nielsen, M. et al , "Inhibition of constitutively activated Stat3 correlates with altered Bcl-2/Bax expression and induction of apoptosis in mycosis fungoides tumor cells," Leukemia (1999) 13:735-738.

Niu et al., "Gene therapy with dominant-negative Stat3 suppresses growth of the murine melanoma B16 tumor in vivo," Cancer Res. (1999) 59:5059-5063.

Porter, A. et al., "Tyrosine kinase receptor-activated signal transduction pathways which lead to oncogenesis," Oncogene (1998) 16:1343-1352.

Rak, J. et al., "Oncogenes as inducers of tumor angiogenesis," Cancer Met. Reviews (1995) 14:263-277 (Abstract only).

Rak, J. et al., "What do oncogenic mutations have to do with angiogenesis/vascular dependence of tumors?" Cancer Res. (2002) 62:1931-1934.

Schindler, C. et al., "Transcriptional responses to polypeptide ligands: the JAK-STAT pathway," Annu. Rev. Biochem. (1995) 64:621-651.

Smithgall, T.E. et al., "Control of myeloid differentiation and survival by Stats," Oncogene (2000) 19:2612-2618.

Sun et al., "Cucurbitacin Q: a selective STAT3 activation inhibitor with potent antitumor activity," Oncogene (2005) 24:3236-3245.

Sun, J. et al., "Cucurbitacin Q: a selective STAT3 activation inhibitor with potent antitumor activity," Oncogene (2005) 1-10.

Sun, X. et al., "Comparison of effects of the tyrosine kinase inhibitors AG957, AG490, and STI571 on BCR-ABL-expressing cells, demonstrating synergy between AG490 and STI571," Blood (2001) 97(7):2008-2015.

Takeda, K. et al., "Targeted disruption of the mouse Stat3 gene leads to early embryonic lethality," PNAS (1997) 94:3801-3804.

Tannock, I.F. et al., The Basic Science of Oncology, Second Edition (Chapter 19, "Experimental Chemotherapy") McGraw-Hill, Inc., New York (1992) 338-340.

Turkson, et al., "A novel platinum compound that inhibits constitutive Stat3 signaling and induces cell cycle arrest and apoptosis of malignant cells," J. Biol. Chem. (2005) 280(38):32979-32988.

Turkson, J. et al., "Stat3 activation by Src induces specific gene regulation and is required for cell transformation," Mol. Cell Biol. (1998) 18:2545-2552.

Wang et al., "Regulation of the innate and adaptive immune responses by Stat3 signaling in tumor cells," Nature Medicine (2004) 10(1):48-54.

Wei, D. et al., "Stat3 activation regulates the expression of vascular endothelial growth factor and human pancreatic cancer angiogenesis and metastasis," Oncogene (2003) 22:319-329.

Wei, L et al., "Interleukin-6 promotes cervical tumor growth by VEGF-dependent angiogenesis via a STAT3 pathway," Oncogene (2003) 22:1517-1527.

Wood, J.M. et al., "PTK787/ZK 222584, a novel and potent inhibitor of vascular endothelial growth factor receptor tyrosine kinases, impairs vascular endothelial growth factor-induced responses and tumor growth after oral administration," Cancer Res. (2000) 60:2178-2189.

Yahata, Y. et al., "Nuclear translocation of phosphorylated Stat3 is essential for vascular endothelial growth factor-induced human dermal microvascular endothelial cell migration and tube formation," J. Biol. Chem. (2003) 278:40026-40031.

United States Patent Office Action for U.S. Appl. No. 11/581,293 dated May 19, 2011 (16 pages).

Burke, W.M. et al., "Inhibition of constitutively active Stat3 suppresses growth of human ovarian and breast cancer cells," Oncogene (2001) 20:7925-7934.

Cheng. J.Q. et al., "Amplification of AKT2 in human pancreatic cancer cells and inhibition of AKT2 expression and tumorigenicity by antisense RNA," Proc. Natl. Acad. Sci. USA (1996) 93:3636-3641.

Dhir, R. et al, "Stat3 activation in prostatic carcinomas," The Prostate (2002) 51:241-246.

Kong, B. et al, "IL-6 antisense-mediated growth inhibition of a choriocarcinoma cell line: an intracellular autocrine growth mechanism," Gynecologic Oncology (1996) 63:78-84.

Lin, J. et al., "The phosphatidylinositol 3'-kinase pathway is a dominant growth factor-activated cell survival pathway in LNCaP human prostate carcinoma cells," Cancer Res. (1999) 59:2891-2897.

Meydan, N. et al., "Inhibition of acute lymphoblastic leukaemia by a Jak-2 inhibitor," Nature (1996) 379:645-648.

Murillo, H. et al., "Role of PI3K signaling in survival and progression of LNCaP prostate cancer cells to the androgen refractory state," Endocrinology (2001) 142(11):4795-4805.

Scherer, L.J. et al., "Approaches for the sequence-specific knockdown of mRNA," Nature Biotech. (2003) 21 (12)1457-1465.

Thabard, W. et al., "IL-6 upregulates its own receptor on some human myeloma cell lines," Cytokine (2001)14 (6):352-356.

Wei, L.-H. et al., "The anti-apoptotic role of interleukin-6 in human cervical cancer is mediated by up-regulation of Mcl-1 through a PI 3-K/Akt pathway," Oncogene (2001) 20:5799-5809.

Yang, L. et al., "Akt/protein kinase B signaling inhibitor-2, a selective small molecule inhibitor of Akt signaling with antitumor activity in cancer cells overexpressing Akt," Cancer Res. (2004) 64:4394-4399.

Yang, L. et al., "Interleukin-6 differentially regulates androgen receptor transactivation via PI3K-Akt, STAT3, and MAPK, three distinct signal pathways in prostate cancer cells," Biochem. Biophys. Res. Comm. (2003) 305:462-469.

United States Office Action for U.S. Appl. No. 11/300,619 dated Sep. 20, 2007.

United States Office Action for U.S. Appl. No. 11/300,619 dated Mar. 10, 2008.

International Search Report and Written Opinion of International Searching Authority for International Application No. PCT/US2005/45225 dated Oct. 18, 2006.

United States Office Action for U.S. Appl. No. 11/102,911 dated Mar. 21, 2008.

International Search Report and Written Opinion of International Searching Authority for International Application No. PCT/US2005/12081 dated Nov. 18, 2005.

Office Action from European Patent Office for European Patent Application No. 05778394.6 dated Jul. 12, 2007.

Office Action from European Patent Office for European Patent Application No. 05778394.6 dated Dec. 18, 2007.

International Search Report and Written Opinion of International Searching Authority for International Application No. PCT/US2006/28108 dated Sep. 12, 2007.

International Search Report and Written Opinion of International Searching Authority for International Application No. PCT/US2006/40457 dated Jul. 16, 2007.

* cited by examiner ic agent. Identification of molecular markers may aid in the development of target-specific therapies and guide the utilization of such specific chemotherapies.

METHODS OF PREDICTING RESPONSIVENESS TO CHEMOTHERAPEUTIC AGENTS AND SELECTING TREATMENTS

CROSS-REFERENCE TO RELATED APPLICATIONS

This application claims priority to U.S. Provisional Application No. 60/700,948, filed Jul. 20, 2005 and U.S. Provisional Application No. 60/596,151, filed Sep. 2, 2005. Both provisional applications are incorporated herein by reference.

STATEMENT REGARDING FEDERALLY SPONSORED RESEARCH OR DEVELOPMENT

This invention was made with U.S. Government support from the National Institutes of Health Grant Nos. CA 82533, CA 55652, R01 102726, U01 CA101222. This work was also supported in part by the Chiles Endowment Biomedical Research Program of the Florida Department of Health and by the H. Lee Moffitt Cancer Center & Research Institute. The Government has certain rights in this invention.

BACKGROUND

Signal transducer and activator of transcription (Stat)-family proteins are latent cytoplasmic transcription factors that convey signals from the cell surface to the nucleus on activation by cytokines and growth factors. See Yu and Jove, Nat Rev 4:97-105 (2004) and Levy and Darnell, Nat Rev Mol Cell Biol 3:651-662 (2002). Engagement of cell surface receptors by polypeptide ligands, such as interleukin-6 (IL-6) or epidermal growth factor, induces tyrosine phosphorylation of Stat proteins by Janus kinase, growth factor receptor tyrosine kinases, and Src family tyrosine kinases. The phosphorylated Stat protein in the activated dimeric form then translocates to the nucleus and regulates expression of genes having Stat-binding sites in their promoters. Under normal physiologic conditions, activation of Stat proteins is rapid, transient and regulates expression of genes that control fundamental biological processes, including cell proliferation, survival, and development.

Numerous studies have detected constitutively active Stat, particularly Stat1, Stat3 and Stat5, in diverse human tumor specimens, including myeloma, leukemia, lymphoma, melanoma and carcinomas from prostate, ovary and head and neck. Persistent Stat activity is established as essential for malignant transformation of cultured cells by many oncogenic signaling pathways. For example, the Src, Janus kinase, and epidermal growth factor receptor family tyrosine kinases are frequently activated in breast cancer cells and induce Stat3 activation. Blocking tyrosine kinase pathways with selective pharmacologic inhibitors results in decreased Stat3 activity, growth inhibition, and apoptosis. Persistent activation of Stat3 and Stat5 in tumor cells has been shown to participate in regulating expression of genes involved in controlling cell cycle progression, apoptosis, and angiogenesis. For instance, an oncogenic mutant of Stat3 induces expression of cyclin D1, Bcl-xL, and c-Myc.

Identification of molecular markers may help guide physicians in the selection of an appropriate chemotherapeutic agent. Identification of molecular markers may aid in the development of target-specific therapies and guide the utilization of such specific chemotherapies.

SUMMARY OF THE INVENTION

In one aspect, methods of predicting responsiveness of cancer cells to chemotherapy are provided. The level of phosphorylated Stat in a cancer cell is measured and compared to the level of phosphorylated Stat in a control. The level of phosphorylated Stat in the cancer cell as compared to the control is predictive of responsiveness to chemotherapy. Kits for performing the methods are also provided and include an antibody capable of binding phosphorylated Stat.

In another aspect, methods of predicting responsiveness of a cancer cell to chemotherapy are provided in which the level of expression of Survivin in a cancer cell is measured. The level of expression of Survivin in the cancer cell is then compared to the level of expression of Survivin in a control. The level of expression of Survivin in the cancer cell as compared to the control is predictive of responsiveness to chemotherapy. Kits for performing the methods are also provided and include an antibody capable of binding Survivin or at least two oligonucleotides capable of amplifying a polynucleotide encoding Survivin or an oligonucleotide capable of hybridizing to Survivin mRNA.

In yet another aspect, methods for selecting a chemotherapeutic treatment for a subject diagnosed with cancer are provided in which the level of phosphorylated Stat in a cancer cell from a subject is measured. The level of phosphorylated Stat in the cancer cell is compared to the level of phosphorylated Stat in a control and the comparison is used to select a chemotherapy treatment for the subject which has an expected benefit based on the level phosphorylated Stat in the cancer cell.

In yet another aspect, methods for treating a subject diagnosed with cancer are provided in which the level of phosphorylated Stat in a cancer cell from the subject is measured. The level of phosphorylated Stat in the cancer cell is compared to the level of phosphorylated Stat in a control and the comparison is used to select a chemotherapy treatment for the subject which has an expected benefit based on the level phosphorylated Stat in the cancer cell. An effective amount of the chemotherapeutic agent is administered to the subject to treat the cancer.

In a still further aspect, methods of modulating Survivin-dependent apoptosis in a cancer cell are provided in which the cell is contacted with an effective amount of a Stat inhibitor.

DETAILED DESCRIPTION

Figure 1:
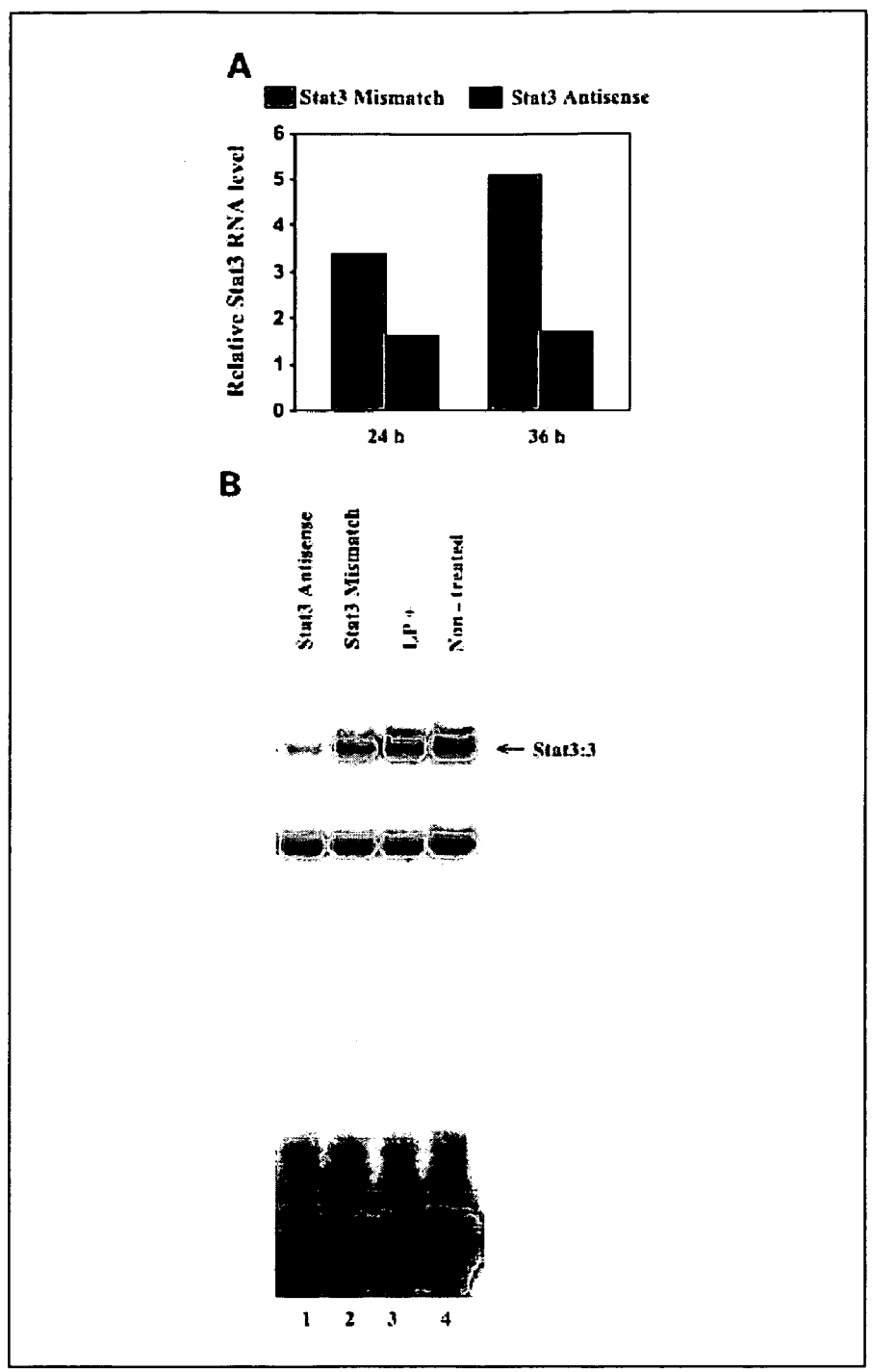
FIG. 1A is a graph representing the decrease in Stat3 mRNA expression after treatment with a Stat3 oligonucleotide.
FIG. 1B is an electrophorectic mobility shift assay demonstrating Stat3 activation is blocked by addition of Stat3 antisense oligonucleotides.

Numerous studies have demonstrated that persistent activation of Stats, particularly Stat1, Stat3 and Stat5a and Stat5b, occurs in a wide variety of tumors, including myeloma, leukemia, lymphoma, melanoma, and carcinoma from prostate, ovary, breast, lung, pancreatic and head and neck. Stats are believed to contribute to oncogenesis by several mechanisms including inhibition of apoptosis, enhancement of cell proliferation, induction of angiogenesis, and suppression of immune responses. The Examples below describe a relationship between activated (phosphorylated) Stat3 and tumor cell responsiveness to various chemotherapeutic agents.

One of skill in the art will appreciate that different cancer cells and different types of cancer respond differently to different types of chemotherapeutic agents. Even within the same type of cancer, such as breast cancer, some cancer cells are more responsive to certain types of chemotherapy than other cancer cells. Currently, physicians and other primary care providers rely on trial and error to determine which chemotherapeutic agents are effective against a particular cancer. Often, cancer cells are resistant to the chemotherapeutic agent and treatment fails to eliminate the cancer. Thus, a diagnostic test capable of predicting responsiveness to a chemotherapeutic agent would be valuable.

The Examples demonstrate that activated Stat3 induces expression of genes involved in blocking apoptosis, such as Survivin, a member of the inhibitor of apoptosis protein (IAP) family, and that apoptosis is induced if Stat3 is blocked. See Li and Altieri, Biochem J 344:305-311 (1999), which is incorporated herein by reference. Furthermore, the levels of activated Stat3 were found to be correlated to the response of breast cancer tumors from women with stage III breast cancer to neoadjuvant chemotherapy with doxorubicin and docetaxel. Tumors having lower levels of activated Stat3 were shown to be more likely to regress in response to chemotherapy than are tumors with high levels of activated Stat3. In non-small cell lung cancer, cells having higher levels of activated Stat3 were found to be more sensitive to treatment with gefitinib, an EGFR tyrosine kinase inhibitor. Taken together the Examples demonstrate a method of predicting responsiveness of cancer cells to a chemotherapeutic agent.

The methods involve measuring the level of phosphorylated Stat in a cancer cell and comparing the level of phosphorylated Stat in the cancer cell to the level of phosphorylated Stat in a control. The level of phosphorylated Stat in the cancer cell as compared to the control is predictive of responsiveness to a chemotherapeutic agent. The responsiveness of the cancer cell to chemotherapy may be decreased or increased depending on the chemotherapeutic agent. The relationship between the level of phosphorylated Stat and the responsiveness of the cancer cell to a particular chemotherapeutic agent can be determined by one of skill in the art. For example, an increased level of phosphorylated Stat is predictive of a decreased level of responsiveness to conventional chemotherapies, such as doxorubicin and docetaxel, or other chemotherapeutic agents that induce apoptosis and indicates treatment with a tyrosine kinase inhibitor.

The methods also include measuring the level of expression of Survivin in a cancer cell and comparing the level of expression of Survivin in the cancer cell to the level of expression of Survivin in a control. The level of expression of Survivin in the cancer cell as compared to the control is predictive of responsiveness to chemotherapy. The responsiveness of the cancer cell to chemotherapy may be decreased or increased depending on the chemotherapeutic agent. The relationship between the level of phosphorylated Stat3 and the responsiveness of the cancer cell to a particular chemotherapeutic agent can be determined by one of skill in the art. For example, an increased level of expression of Survivin is predictive of a decreased level of responsiveness to conventional chemotherapies such as doxorubicin and docetaxel and may indicate treatment with a tyrosine kinase inhibitor.

A cancer cell is responsive to a chemotherapeutic agent if the chemotherapeutic agent induces apoptosis, decreases cell proliferation, or induces an immune response against the cancer cell. Responsiveness of a cancer cell to a chemotherapeutic agent may also be measured as a reduction in tumor size, or inhibition of angiogenesis. Responsiveness to a chemotherapeutic agent may be measured after the therapy is completed by methods known to those of skill in the art including, but not limited to, palpation, imagery and surgical removal. In the Examples, the residual tumor was surgically removed after chemotherapy in individuals with stage III breast cancer and the size of the tumor was compared to the size of the tumor by palpation prior to chemotherapy.

Responsiveness to the chemotherapeutic agent may be either an in vitro response of a cancer cell or an in vivo clinical response of a cancer in a subject. Cancer includes, but is not limited to, tumors, cancer cells and metastases. The responsiveness of a cancer cell to treatment with a chemotherapeutic agent may be assessed in a variety of ways known to those of skill in the art, including, but not limited to, proliferation assays and apoptosis assays. For example, proliferation assays, include but are not limited to $^3$H-thymidine incorporation, trypan blue exclusion assays and MTT assays. Apoptosis assays include, but are not limited to, TUNEL, PARP cleavage, and DNA fragmentation. In vivo assays for responsiveness are also known to those of skill in the art and include, but are not limited to, assays for assessing the size and metastasis of a cancerous tumor.

Clinical response of a tumor to treatment with a chemotherapeutic agent may be assessed by measuring the size of the tumor. One of ordinary skill in the art would understand how to determine the size of a tumor. For example the size may be determined by palpation or imaging, such as a CT scan or an MRI. A complete clinical response is defined as disappearance of all measurable tumor by clinical exam, such as by palpation or imaging. A partial clinical response is defined as a reduction by at least 50% of the size of the tumor. Progression of a tumor is defined as an increase in the size of the tumor or the appearance of any new lesions. Stable disease is defined as a response that did not meet the partial response or progression criteria.

Pathologic response is determined at the time of surgery, and a response is classified as a complete pathologic response or partial pathologic response based on the residual tumor size after chemotherapy. A complete pathologic response is defined as substantially no evidence of tumor in or around the original site. In the Examples, pathologic response was determined in the breast and separately in the axillary lymph nodes in those patients who were known to have documented positive lymph nodes by palpation, fine needle aspiration, or sentinel lymph node mapping prior to chemotherapy. A partial pathologic response is defined as evidence of tumor, but of a smaller size than the tumor prior to chemotherapy.

The methods in accordance with the present invention are useful in predicting responsiveness of cancers to a particular chemotherapeutic agent based on a statistical analysis as described in the Examples. The Student's t test was used if the data followed a normal distribution and the Wilcoxon Mann-Whitney test was used if the normality assumption was not met. All tests were two-sided and declared significant at the 5% level. Cancers having high levels of phosphorylated Stat or high levels of Survivin relative to non-cancerous control cells are less likely to respond to some chemotherapy agents such as the taxane derivatives or anti-cancer agents such as doxorubicin, but are more likely to respond to chemotherapeutic agents which are inhibitors of tyrosine phosphorylation or other signaling pathways such as Stat inhibitors or EGFR tyrosine kinase inhibitors. For example, FIG. 8 in Example 7 demonstrates that individuals with cancer cells having high levels of phosphorylated Stat3 are less likely to mount a complete pathologic response to the breast cancer after treatment with doxorubicin and docetaxel than individuals whose cancer cells have lower levels of phosphorylated Stat3. On the other hand, FIGS. 9A and 9B in Example 10 demonstrate that cancer cells having higher levels of phosphorylated Stat3, such as H3255, were more susceptible to treatment with gefitinib than cell lines having relatively low levels of phosphorylated Stat3, such as H1299.

The methods in accordance with the present invention may be used to predict responsiveness of a cancer to a chemotherapeutic agent. The subject diagnosed with cancer may be human or a non-human mammal. The methods allow prediction of responsiveness of a number of different cancers including, but not limited to breast cancer, lung cancer, ovarian cancer, head and neck cancer, melanoma, lymphoma, leukemia, multiple myeloma, prostrate cancer, gastric cancer, colon cancer and pancreatic cancer.

The methods in accordance with the present invention may be used to predict responsiveness of cancers to various chemotherapeutic regimens. In the Examples, the methods are used to enable prediction of responsiveness of breast cancer to neoadjuvant therapy with doxorubicin and docetaxel and non-small cell lung cancer to EGFR tyrosine kinase inhibitor therapy. Neoadjuvant therapy refers to the use of chemotherapy or hormonal therapy as the initial treatment of a primary malignant tumor followed by surgery to remove the tumor.

The methods may be used to predict responsiveness to chemotherapeutic agents delivered by any means known to those of skill in the art. The methods can also be used to predict responsiveness of cancers to other chemotherapeutic agents including, but not limited to, Stat inhibitors and Survivin inhibitors. For example, Stat3 inhibitors include, but are not limited to, RNAi directed against Stat3 mRNA and those identified in the following publications: Turkson et al., J Biol Chem 276:45443-455 (2001); Turkson et al., Mol Cancer Ther 3:261-69 (2004); Sun et al., Oncogene 24:3236-3245 (2005); and Turkson et al., Mol Cancer Ther (in revision), which are incorporated herein by reference.

Chemotherapeutic agents include, but are not limited to, alkylating agents such as busulfan, cisplatin, carboplatin, chlorambucil, cyclophosphamide, ifosfamide, dacarbazine (DTIC), mechlorethamine (nitrogen mustard), melphalan, and temozolomide; nitrosoureas such as carmustine (BCNU) and lomustine (CCNU); antimetabolites such as 5-fluorouracil, capecitabine, 6-mercaptopurine, methotrexate, gemcitabine, cytarabine (ara-C), fludarabine, and pemetrexed; anthracyclines such as daunorubicin, doxorubicin (Adriamycin), epirubicin, idarubicin, and mitoxantrone; topoisomerase I or II inhibitors such as topotecan and irinotecan, etoposide (VP-16) and teniposide; mitotic inhibitors such as the taxanes (paclitaxel, docetaxel) and the vinca alkaloids (vinblastine, vincristine, and vinorelbine); L-asparaginase, dactinomycin, thalidomide, tretinoin, gefitinib, and erlotinib.

The level of phosphorylated Stat may be measured in a variety of ways including, but not limited to, immunohistochemistry, electrophorectic mobility shift assay, Western blot, and enzyme-linked immunosorbent assay (ELISA). Each of these assays is capable of differentiating between phosphorylated Stat and its unactivated, non-phosphorylated form. One of skill in the art will appreciate that for diagnostic purposes, a measurement system adaptable for high throughput analysis such as ELISA, or a spectroscopic or enzymatic assay would be suitable.

The level of expression of Survivin may be measured at either the protein or RNA level by any method known in the art including, but not limited to, immunohistochemistry, Western blot, ELISA, microarray, rt-PCR and Northern blot. One of skill in the art will appreciate that for diagnostic purposes a measurement system adaptable for high throughput analysis such as ELISA, or a spectroscopic or enzymatic assay would be suitable.

The level of phosphorylated Stat and the level of expression of Survivin may be measured in a cancer cell or a tumor from a subject diagnosed with cancer and in a control. The control may be non-cancerous cells or non-cancerous tissues or cancer cells or cancerous tissues with known responsiveness to chemotherapy. In another embodiment, the control may be a cell line, such as H460, H1299, H549, H358, or MDA-MB-361 cells, having a reference level of phosphorylated Stat or a reference level of expression of Survivin. The control may also be a reference chart for comparison of levels of phosphorylated Stat and expression of Survivin.

In one embodiment, the control may be a non-cancerous control cell obtained from the same subject as the cancer cell or obtained from a different subject. The control may be obtained by any method known to those of skill in the art including, but not limited to, biopsy, fine needle aspiration, and surgical resection or removal.

In another embodiment, the control is a set of samples containing known amounts of phosphorylated Stat or a known level of expression of Survivin. The control samples, containing various levels of phosphorylated Stat or levels of expression of Survivin, have known responsiveness to chemotherapy such that the control samples form a curve of responsiveness as it relates to the level of phosphorylated Stat or the level of expression of Survivin. Such a set of control samples provides adequate relative information that a primary care provider can compare the level of phosphorylated Stat or the level of expression of Survivin in a cancer from a subject to the respective level of phosphorylated Stat or level of expression of Survivin in the control samples to make an informed prediction of the responsiveness of the cancer to various types of chemotherapy.

Methods for selecting a chemotherapeutic agent for a subject diagnosed with cancer are also provided. The methods involve measuring the level of phosphorylated Stat or the level of expression of Survivin in a cancer cell obtained from a subject and comparing the level of phosphorylated Stat or the level of expression of Survivin in the cancer cell to the level of phosphorylated Stat or the level of expression of Survivin, respectively, in a control. This information is then used to determine the chemotherapeutic agent for the subject. Finally, an effective amount of the chemotherapeutic agent is administered to the subject to treat the cancer.

If a cancer is predicted to be less responsive or more responsive to a particular chemotherapeutic agent by the methods described above, then the chemotherapy treatment provided to the subject can be tailored such that the subject is given the chemotherapy treatment to which the cancer is likely to respond. In the Examples, non-small cell lung cancer cells having increased levels of phosphorylated Stat3 were demonstrated to have increased sensitivity to EGFR tyrosine kinase inhibitors. Thus subjects with non-small cell lung cancer which demonstrate increased levels of phosphorylated Stat3 should be treated with an effective amount of an EGFR tyrosine kinase inhibitor. In patients with breast cancer, cancer cells having an increased level of phosphorylated Stat3 and increased expression of Survivin were less likely to respond to neoadjuvant chemotherapy with doxorubicin and docetaxel. Thus, a subject with breast cancer having an increased level of phosphorylated Stat3 or of Survivin should be treated with an alternative chemotherapy, such as Src inhibitors or Stat3 inhibitors. An increased level of phosphorylated Stat3 in a cancer cell as compared to a control is indicative of sensitivity of the cancer to EGFR tyrosine kinase inhibitors, Stat3 inhibitors and Src kinase inhibitors.

Treatment or treating a cancer includes, but is not limited to, reduction in cancer growth or tumor burden, enhancement of an anti-cancer immune response, induction of apoptosis of cancer cells, inhibition of angiogenesis, enhancement of cancer cell apoptosis, and inhibition of metastases. Administration of an effective amount of a chemotherapeutic agent to a subject may be carried out by any means known in the art including, but not limited to intraperitoneal, intravenous, intramuscular, subcutaneous, transcutaneous, oral, nasopharyngeal or transmucosal absorption. The specific amount or dosage administered in any given case will be adjusted in accordance with the specific cancer being treated, the condition, including the age and weight, of the subject, and other relevant medical factors known to those of skill in the art.

Dosages for a particular subject can be determined using conventional considerations known to those of skill in the art, including but not limited to a subject's age, body weight, general state of health, diet, the timing and mode of administration, the rate of excretion, other medicaments used in combination and the severity and invasiveness of the cancer. For example, between 60 and 90 milligrams per square meter of doxorubicin may be administered via a single intravenous (IV) injection every 21 days. Suitably, 75 to 85 mg/m$^2$ doxorubicin may be administered. Alternately, between 20 and 30 milligrams of doxorubicin per square meter per day may be given via IV for three days every three to four weeks. Alternately, 20 milligrams of doxorubicin per square meter may be given via IV weekly. The dose of doxorubicin used depends upon which regimen for cancer therapy is being followed. Docetaxel may be administered intravenously, in a dose that ranges from 60-100 mg/m$^2$, over one hour, once every three weeks. Suitably, docetaxel may be administered in a dose of 70-90 mg/m$^2$, or from 70-80 mg/m$^2$. Gefitinib may be taken orally, once daily at 250 mg/day for an adult.

Methods are also provided for modulation of Survivin-dependent apoptosis in a cancer cell. The cancer cell is contacted with an effective amount of Stat3 inhibitor to induce apoptosis. Stat3 inhibitors include, but are not limited to, those identified by the methods described above and those identified in the following publications: Turkson et al., J Biol Chem 276:45443-455 (2001); Turkson et al., Mol Cancer Ther 3:261-69 (2004); Sun et al., Oncogene 24:3236-3245 (2005); and Turkson et al., Mol Cancer Ther (in revision) which are incorporated herein by reference. As demonstrated in the Examples below, activated Stat3 induces expression of Survivin and Survivin in turn blocks apoptosis. Therefore, blocking or reversing Stat3 activation and phosphorylation results in decreased expression of Survivin and allows induction of apoptosis in some cancer cells. The following examples are provided to assist in further understanding of the invention. The particular materials and methods employed are considered to be illustrative of the invention and are not meant to be limiting on the scope of the claims.

EXAMPLES

Example 1

Stat3 Antisense Oligonucleotides Block Expression and Activation of Stat3

The human breast cancer cell line MDA-MB-435s, harbors activated Stat3. The cells were grown in DMEM supplemented with 10% fetal bovine serum, 100 units/mL penicillin, and 100 μg/mL streptomycin. The cells were transfected with Stat3 antisense or mismatch oligonucleotides using Lipofectamine-Plus as described by the supplier (Life Technologies, Grand Island, N.Y.). The Stat3 antisense (5' GCTCCAGCATCTGCTGCTTC-3') (SEQ ID NO: 1) and control mismatch (5'GCTCCAATACCCGTTGCTTC-3') (SEQ ID NO: 2) oligonucleotides were synthesized using phosphorothioate chemistry. To increase stability, oligonucleotides were synthesized with 2'-O-methoxyethyl modification of the five or three underlined terminal nucleotides. The final concentration for Stat3 antisense and control mismatch oligonucleotides was 250 mmol/L. Twenty-four and 36 hours after transfection, the mRNA levels and DNA-binding activities of Stat3 were measured by RNase protection and electrophoretic mobility shift (EMSA) assays, respectively.

RNase protection assay. Total RNA was isolated from MDA-MB-435s cells using the RNAeasy mini kit (Qiagen, Valencia, Calif.). RNase protection assays were carried out with the Riboquant hStress-1 template set containing Bcl-xL and Mcl-1 probes or custom-made multiprobe templates containing Stat3 probes (BD PharMingen, San Diego, Calif.). Briefly, the multiprobe templates were synthesized by in vitro transcription with incorporation of [$^{32}$P]dUTP and purified on Quick Spin RNA columns (Roche Applied Science, Indianapolis, Ind.). Labeled probe ($1 \times 10^6$ cpm) was hybridized with 10 μg of total RNA through a temperature gradient of 90° C. to 56° C. over a 16-hour period. Unprotected probe was removed by RNase digestion at 30° C. for 1 hour followed by separation of protected RNA fragments on a 5% polyacrylamide-urea gel and detection using autoradiography.

Nuclear extract preparation and EMSA. Nuclear extracts were prepared as previously described by Yu et al., Science 269:81-83 (1995), which is incorporated herein by reference, by high-salt extraction into 30 to 70 μL buffer [20 mmol/L HEPES (pH 7.9), 420 mmol/L NaCl, 1 mmol/L EDTA, 20% glycerol, 20 mmol/L NaF, 1 mmol/L Na$_3$VO$_4$, 1 mmol/L Na$_4$P$_2$O$_7$, 1 mmol/L DTT, 0.5 mmol/L phenylmethylsulfonyl fluoride, 0.1 μmol/L aprotinin, 1 μmol/L leupeptin, and 1 μmol/L antipain]. For EMSA, 5 μg of total nuclear protein were used for each lane. EMSA was done using a $^{32}$P-labeled oligonucleotide probe containing a high-affinity cis-inducible element (hSIE, m67 variant) derived from the c-fos gene promoter (sense strand 5'AGCTTCATTTCCCGTAAATC-CCTA-3') (SEQ ID NO: 3) that binds activated Stat3 proteins. Following incubation of radiolabeled probes with nuclear extracts, protein-DNA complexes were resolved by nondenaturing PAGE and detected by autoradiography. Stat3 protein was supershifted in the EMSA by preincubation with Stat3 antibody (C-20X, Santa Cruz Biotechnology, Santa Cruz, Calif.).

FIG. 1A shows that Stat3 antisense diminished Stat3 mRNA expression compared with the mismatch oligonucleotides. The decrease in mRNA expression was accompanied by a significant decrease in Stat3 DNA-binding activity (FIG. 1B).

Example 2

Direct Blocking of Stat3 Induces Apoptosis in Breast Cancer Cells

To assess whether apoptosis was occurring in the cells after blocking of Stat3 the cells were examined microscopically and a TUNEL assay and poly-(ADP)-ribose polymerase (PARP) cleavage assay were performed.

In situ terminal deoxyribonucleotidyl transferase-mediated dUTP nick end labeling and cellular proliferation assays. MDA-MB-435s and MDA-MB-231 cells were transfected with antisense or control mismatch oligonucleotides. After 48 hours, cells were labeled for apoptotic DNA strand breaks by terminal deoxyribonucleotidyl transferase-mediated dUTP nick end labeling (TUNEL) reaction using an in situ cell death detection assay (Roche Applied Science, Indianapolis, Ind.) according to the instructions of the supplier. TUNEL-positive nuclei were counted and the apoptotic index was expressed as the number of apoptotic cells in one microscopic field. To determine cellular viability, cells were harvested by trypsinization and counted by trypan blue exclusion assay at 24 and 48 hours after transfection. All experiments were done in triplicate.

Western blot analyses. Cells were lysed in a buffer containing 10 mmol/L Tris-HCl (pH 8.0), 150 mmol/L NaCl, 1% NP40, 0.5% sodium deoxycholate, 0.1% SDS, 1 mmol/L EDTA (pH 8.0), 2 mmol/L phenylmethylsulfonyl fluoride, 2 μg/mL aprotinin, 2 μg/mL leupeptin, and 1 mmol/L Na$_3$VO$_4$. For Western blot analyses, 30 μg of total extracted proteins were applied per lane before SDS-PAGE. Following transfer to nitrocellulose membranes, protein expression levels were detected using polyclonal anti-poly-(ADP-ribose) polymerase antibodies (Cell Signaling Technology, Beverly, Mass.). The expression of β-actin (Sigma-Aldrich, St. Louis, Mo.) was used as a normalization control for protein loading.

Figure 2:
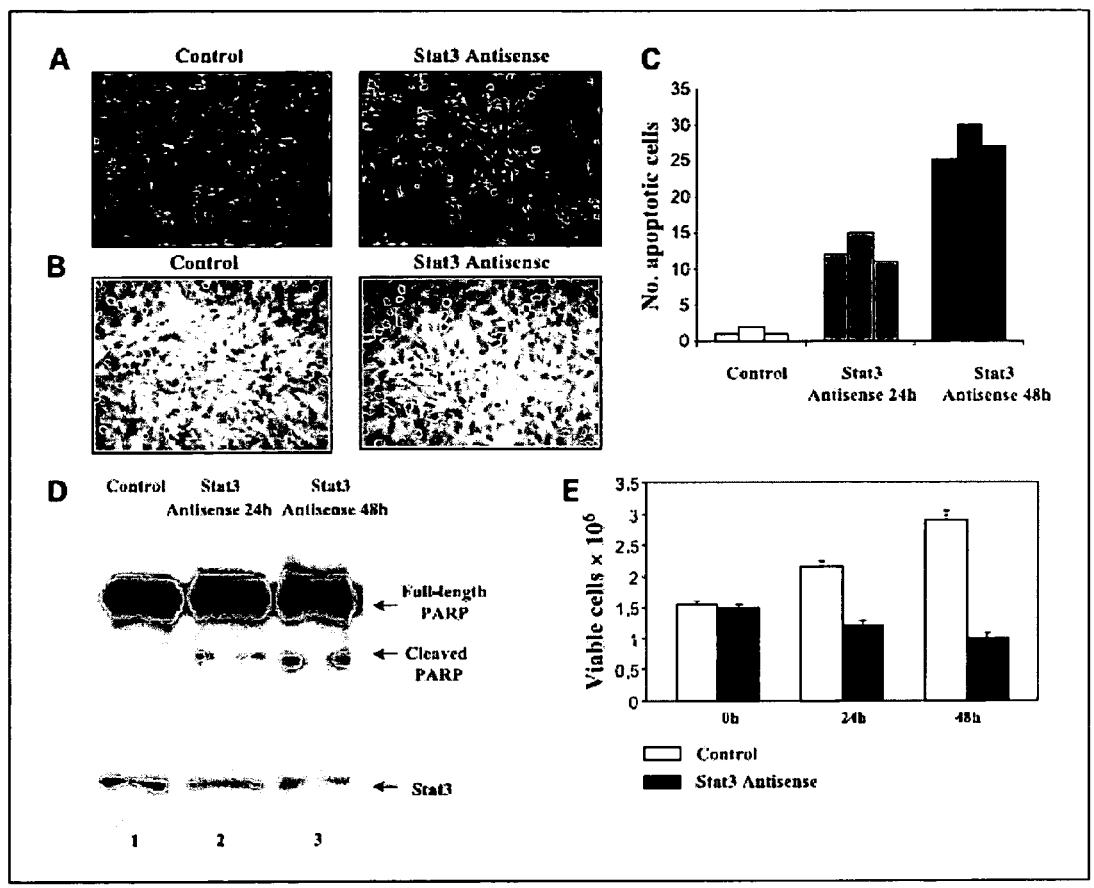
FIG. 2A shows light micrographs of normal cells and those treated with Stat3 antisense oligonucleotides.
FIG. 2B shows light micrographs of an in situ TUNEL assay.
FIG. 2C is a graph showing the results of the TUNEL assay.
FIG. 2D is a Western blot analysis detecting PARP cleavage as an indicator of apoptosis.
FIG. 2E is a graph of viable cells after treatment with Stat3 antisense as compared to control cells.

Incubation of cells with Stat3 antisense oligonucleotides for up to 48 hours resulted in a marked increase in vacuolated cells and cellular debris (FIG. 2A), indicative of apoptotic cell death. The occurrence of apoptosis was confirmed by in situ TUNEL assay (FIGS. 2B and C) and by cleavage of poly-(ADP-ribose) polymerase at 48 hours after treatment with antisense oligonucleotides (FIG. 2D). FIG. 2E shows that treatment with Stat3 antisense oligonucleotide also induced significant growth inhibition as measured by trypan blue exclusion after 24 or 48 hours of incubation. Both apoptosis and inhibition of cellular proliferation correlated with blockade of Stat3 expression and activation (See, e.g., FIG. 1 and Gritsko et al., Clin. Cancer Res. 12:11-19 (2006) which is incorporated herein by reference).

Example 3

Inhibition of Stat3 Decreases Expression of Survivin in Breast Cancer Cells

Microarray gene expression profiling analyses were completed to assess the gene expression changes associated with blockade of Stat3 activity. Five micrograms of total RNA collected from MDA-MB-435s cells treated with antisense or control mismatch oligonucleotides for 24 hours served as the mRNA sources for microarray analysis. The poly(A) mRNA was specifically converted to cDNA and then amplified and labeled with biotin following the procedure initially described by Van Gelder et al., Proc. Natl. Acad. Sci. USA 87:1663-67 (1990) which is incorporated herein by reference. Hybridization with the biotin-labeled DNA, staining, and scanning of the microarray chips followed the prescribed procedure outlined in the Affymetrix technical manual.

The oligonucleotide probe arrays were Human Genome U133A chips (Affymetrix, Santa Clara, Calif.). Scanned output files were visually inspected for hybridization artifacts and then analyzed using Affymetrix Microarray MAS 5.0 software. The MAS 5.0 software identifies the increased and decreased genes between any two samples with a statistical algorithm that assesses the behavior of oligonucleotide probe sets designed to detect the same gene. Probe sets that yielded a change at $P < 0.0045$ were identified as changed (increased or decreased). In addition, the data were processed using robust multiarray analysis as described by Bolstad et al., Bioinformatics 19:185-93 (2003) which is incorporated herein by reference in its entirety. Genes that were significantly changed in their expression were identified. Empirical estimates of the null distribution were determined using per-mutation analysis, thereby controlling the number of false positives. The significance analysis of microarrays (as described by Tusher et al., Proc Natl Acad Sci USA 98:5116-21 (2001), which is incorporated herein by reference) implements this approach to address the multiple testing problem and was also applied to the data analysis. Genes were considered changed if consistent behavior (increase or decrease) was observed in each of three replicate experiments based on analyses of data by the multiple methods described above.

The biological functions of the genes identified were diverse, but included several apoptosis-related genes. Microarray analysis did not reveal consistent decreases in the expression of any Bcl-2 family proteins in antisense oligonucleotide-treated breast cancer cells (See Table 1). In contrast, expression of Survivin, which is a member of the IAP family of antiapoptotic genes, was found to be diminished by microarray analysis as confirmed below by independent molecular approaches. The microarray analysis revealed no change in other IAP family members including X-linked IAP, cellular IAP-1, and cellular IAP-2 (Table 1).

TABLE 1

| Probe | Score(d) | Gene Name | Gene Symbol | Function | Accession Number | Locus Link |
|---|---|---|---|---|---|---|
| 218856_at | −2.7907752 | Tumor necrosis factor receptor superfamily member 21 | TNFRSF21 | This receptor has been shown to activate NF-kappaB and MAPK8/JNK; and induce cell apoptosis | NM_104452 | 27242 |
| 215714_s_at | −2.6432594 | SWI/SNF related, matrix associated, actin dependent regulator of chromatin, subfamily a, member 4 | SMARCA4 | The encoded protein is part of the large ATP-dependent chromatin remodeling complex SNF/SW1, which is required for transcriptional activation of genes normally repressed by chromatin. This protein can also bind BRCA1, as well as regulate the expression of the sumorigenic protein CD44. | NM_003072 | 6597 |
| 218308_at | −2.547692 | Transforming acidic coiled-coil containing protein 3 | TACC3 | This gene may be involved in cell growth and differentiation. Expression of this gene is up-regulated in some cancer cell lines. | NM_006342 | 10460 |
| 209953_s_at | −2.5136819 | CDC37 cell division cycle 37 homolog (S. cerevisiae) | CDC37 | This protein is a molecular chaperone with specific function in cell signal transduction. It has been shown to form complex with Hsp90 and a variety of protein kinases including CDK4, CDK6, SKR, RAF-1, MOK, as well as eIF2 alpha kinases. It is playing a critical role in directing HSP90 to its target kinases | NM_007065 | 11140 |
| 45572_s_at | −2.5099301 | Golgi associated, gamma adaptin ear containing, ARF binding protein 1 | GGA1 | The ubiquitous coat protein that regulate the trafficking of proteins between the trans-Golgi network and the lysosome. Proteins from this family share an amino-terminal VHS domain which mediates sorting of the mannose 6-phosphate receptors at the trans-Golgi network. | NM_013365 | 26088 |
| 202039_at | −2.3578191 | TCFB1-induced anti-apoptotic factor 1 or | T1AF1 | This gene is induced by TGF-beta and mediates some of its | NM_004740 | 9220 |

TABLE 1-continued

| Probe | Score(d) | Gene Name | Gene Symbol | Function | Accession Number | Locus Link |
|---|---|---|---|---|---|---|
| | | Myosin XVIIIA | MYO18A | effects T1AF1 appears to participate in the nuclear translocation of phosphorylated p53. This gene shares its 3' most exon with T1AF1, it encodes an intermediate filament protein that is localized to the ER-Golgi complex in most cells, an alternately spliced transcript has been detected in hematopoietic cells that encodes a cytosolic form. | NM_078471 | 399687 |
| 202395_at | −2.3187223 | N-ethylmaleimide-sensitive factor | NSF | Nitric oxide regulates exocytosis by S-nitrosylation of NSF, Binding of NSF to GluR2-containing AMPARs stabilizes these receptors in the synaptic membrane and impedes their regulated endocytosis. | NM_006178 | 4905 |
| 203318_s_at | −2.2699704 | Zinc finger protein 148 (pHz-52) | ZNF148 Alternate symbol ZBP-89 | Regulates gene transcription of the T-cell receptor, beta enolase and gastrin; interaction with Stat3 may be crucial for overcoming the repressor effects of ZBP-89, which suggests a novel mode for Stat3 activation. Co-localized with p53 in the nucleus in hepatocellular carcinoma suggesting that ZBP-89 may play a role in the nuclear accumulation of the p53 protein. | NM_021964 | 7707 |
| 207556_s_at | −2.2377738 | Discylglycerol kinase, zeta | DGKZ | The protein may attenuate protein kinase C activity by regulating diacylglycerol levels in intracellular signaling cascade and signal transduction | NM_003646 | 8525 |
| 208992_s_at | −2.1666872 | Signal transducer and activator of transcription 3 (acute-phase response factor) | STAT3 | This protein mediates the expression of a variety of genes in response to cell stimuli, and thus plays a key role in many cellular processes such as cell growth and apoptosis. | NM_003150 NM_139276 | 6774 |
| 221718_s_at | −2.0686379 | A kinase anchor protein, 13 | AKAP13 | A-kinase anchor proteins are structurally diverse proteins with the common function of binding to the regulatory submit of protein kinase A and confine the enzyme to discrete locations within the cell. | NM_006738 | 11214 |

TABLE 1-continued

| Probe | Score(d) | Gene Name | Gene Symbol | Function | Accession Number | Locus Link |
|---|---|---|---|---|---|---|
| 208579_x_at | 6.9484441 | Histone 1, H2bk (This probeset may also recognize other H2b isoforms) | HIST1H2BK | This member of the histone H2B family gene is found in the histone microcluster on chromosome 6p21.33. | NM_017445.1 | 85236 |
| 213704_at | 6.5143241 | Rab geranylgeranyltransferase, beta subunit | RABGGTB | This gene encodes one subunit of the protein involved in the geranylgeranylation of various proteins. | NM_004582 | 5876 |
| 218276_s_at | 6.0481899 | Salvador homolog 1 (*Drosophila*) | SAV1 | This gene encodes a protein, which contains 2WW domains and a coiled-coil region. WW domain-containing proteins are found in all eukaryotes and play an important role in the regulation of a wide variety of cellular functions such as protein degradation, transcription, and RNA splicing. | NM_021818 | 60485 |
| 200733_s_at | 5.8891785 | Protein tyrosine phosphatase type IVA, member 1 | PTP4A1 | PTPs are cell molecules that play regulatory roles in a variety of cellular processes. Overexpression of this gene in mammalian cells conferred a transformed phenotype, which implicated its role in the tumorigenesis. | NM_003463 | 7803 |
| 209310_s_at | 5.6890816 | Caspase 4, apoptosis-related cysteine protease | CASP4 | Sequential activation of caspases plays a central role in the execution-phase of cell apoptosis. This caspase is able to cleave and activate its own, as well as caspase 1, precursor proteins. When overexpressed, this gene has been shown to induce cell apoptosis. | NM_001225 NM_033306 NM_033307 | 837 |
| 203403_s_at | 4.8716965 | Ring finger protein (C3H2C3 type) 6 | RNF6 | Deletions and mutations in this gene were detected in esophageal sqamous cell carcinoma, suggesting that this protein may be a potential tumor suppressor. Studies of the mouse counterpart suggested a role of this protein n the transcription regulation that controls germinal differentiation. | NM_005977 NM_183043 NM_183044 | 6049 |
| 213134_x_at | 3.6197099 | BTG family, member 3 | BTG3 | The protein encoded by this gene is a member of the BTGTob family. This family has structurally related proteins that appear to have antiproliferative properties. | NM_006806 | 10950 |

TABLE 1-continued

| Probe | Score(d) | Gene Name | Gene Symbol | Function | Accession Number | Locus Link |
|---|---|---|---|---|---|---|
| 203725_at | 3.1865638 | Growth arrest and DNA-damage-inducible, alpha | GADD45A | This gene is a member of a group of genes whose transcript levels are increased following stressful growth arrest conditions and treatment with DNA-damaging agents. The protein encoded by this gene responds to environmental stresses by mediating activation of the P38/JNK pathway via MTK1/MEKK4 kinase. The DNA damage-induced transcription of this gene is mediated by both p53-dependent and -independent mechanisms. The p53-independent induction of a GADD45 mediates tumor-suppressing activity of 1,25 dihydroxyvitamin D3 in human ovarian cancer cells. | NM_001924 | 1647 |

Figure 3:
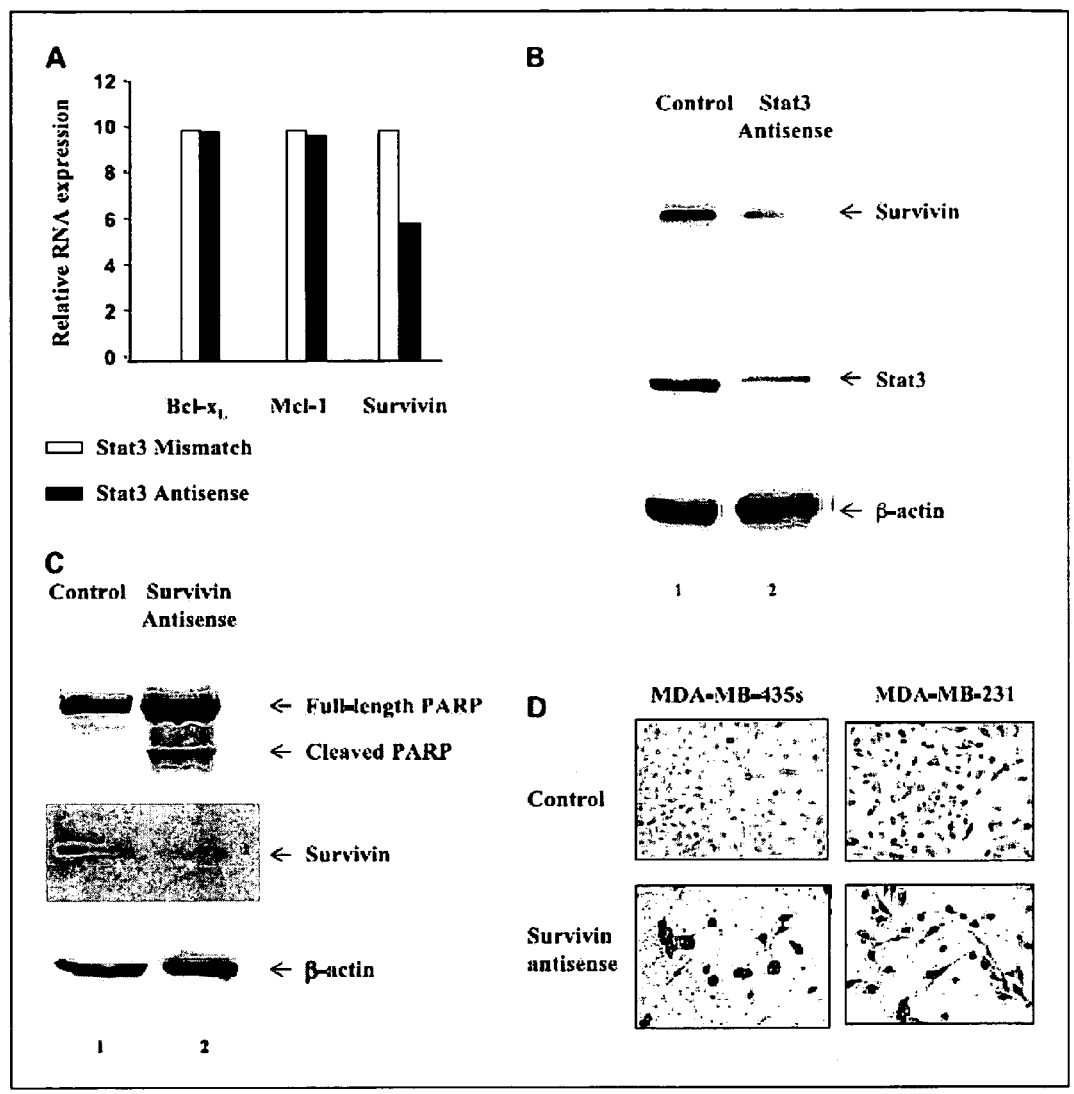
FIG. 3A is a graph of an RNase protection assay for anti-apoptotic genes expressed in a breast cancer cell line after treatment with the Stat3 antisense oligonucleotide.
FIG. 3B is a Western blot analysis showing expression of Stat3 and Survivin after treatment with Stat3 antisense oligonucleotides.
FIG. 3C is a Western blot analysis for PARP cleavage and Survivin expression in breast cancer cells.
FIG. 3D is a light micrograph of a TUNEL assay.

The microarray data were validated using an RNase protection assay using a Survivin probe (BD PharMingen, San Diego, Calif.) as described above. Results showed a decrease in mRNA expression of Survivin, but not of Bcl-xL or Mcl-1, in antisense oligonucleotide-treated breast cancer cells (FIG. 3A). The correlation between Stat3 and Survivin protein expression was further confirmed by Western blot analysis. Protein expression levels were detected using polyclonal anti-Stat3 (Santa Cruz Biotechnology, Santa Cruz, Calif.) and polyclonal anti-Survivin (Alpha Diagnostics International, San Antonio, Tex.) antibodies. The data demonstrated decreased Survivin expression in breast cancer cells that are treated with Stat3 antisense oligonucleotide (FIG. 3B).

Activated Stat3 signaling promoted the survival of breast tumor cells, through an unknown mechanism. Because activated Stat3 was shown to induce expression of Survivin and Survivin is a member of the IAP family, the ability of Survivin expression to protect breast cancer cells from apoptosis was investigated. Antisense oligonucleotides directed against Survivin (5'-CCCAGCCTTCCAGCTCCTTG-3') (SEQ ID NO: 4) were synthesized using phosphorothioate chemistry as described above and were used at a final concentration of 300 nmol/L. MDA-MB-435s and MDA-MB-231 cells were transfected with antisense oligonucleotides directed against Survivin as described above. Poly-(ADP-ribose) polymerase cleavage (FIG. 3C) and in situ TUNEL staining (FIG. 3D) were evident following inhibition of Survivin expression, indicative of apoptosis. Thus, expression of the antiapoptotic protein Survivin is associated with constitutive Stat3 activity and survival in breast cancer cells.

Example 4

Stat3 Directly Binds to and Regulates the Survivin Promoter

To determine whether Stat3 regulates Survivin promoter activity, transient transfection studies with a luciferase reporter gene driven by the human Survivin promoter were completed. The reporter pGL2-Survivin encodes the Survivin gene promoter driving expression of firefly luciferase in pGL2 (Promega, Madison, Wis.). Expression vectors for v-Src (pMvSrc) and Stat3 (pVRStat3) have been previously described by Turkson et al., Mol Cell Biol. 18:2545-52 (1998), which is incorporated herein by reference. Cytosolic extract preparation and luciferase assays were done as previously described by Turkson et al., Mol Cell Biol 18:2545-52 (1998). Briefly, cells were lysed in 0.1 mL of low-salt HEPES buffer [10 mmol/L HEPES (pH 7.8), 10 mmol/L KCl, 0.1 mmol/L EGTA, 0.1 mmol/L, EDTA, 1 mmol/L phenylmethylsulfonyl fluoride, 1 mmol/L DTT, and 20 μL of 10% NP40]. After centrifugation (10,000×g, 1 minute, 4° C.), cytosolic supernatant was used for luciferase assays as described by the vendor (Promega). Experiments were done in triplicate and the average values were determined. To control for transfection efficiency, firefly luciferase values were normalized to the values for β-galactosidase.

Figure 4:
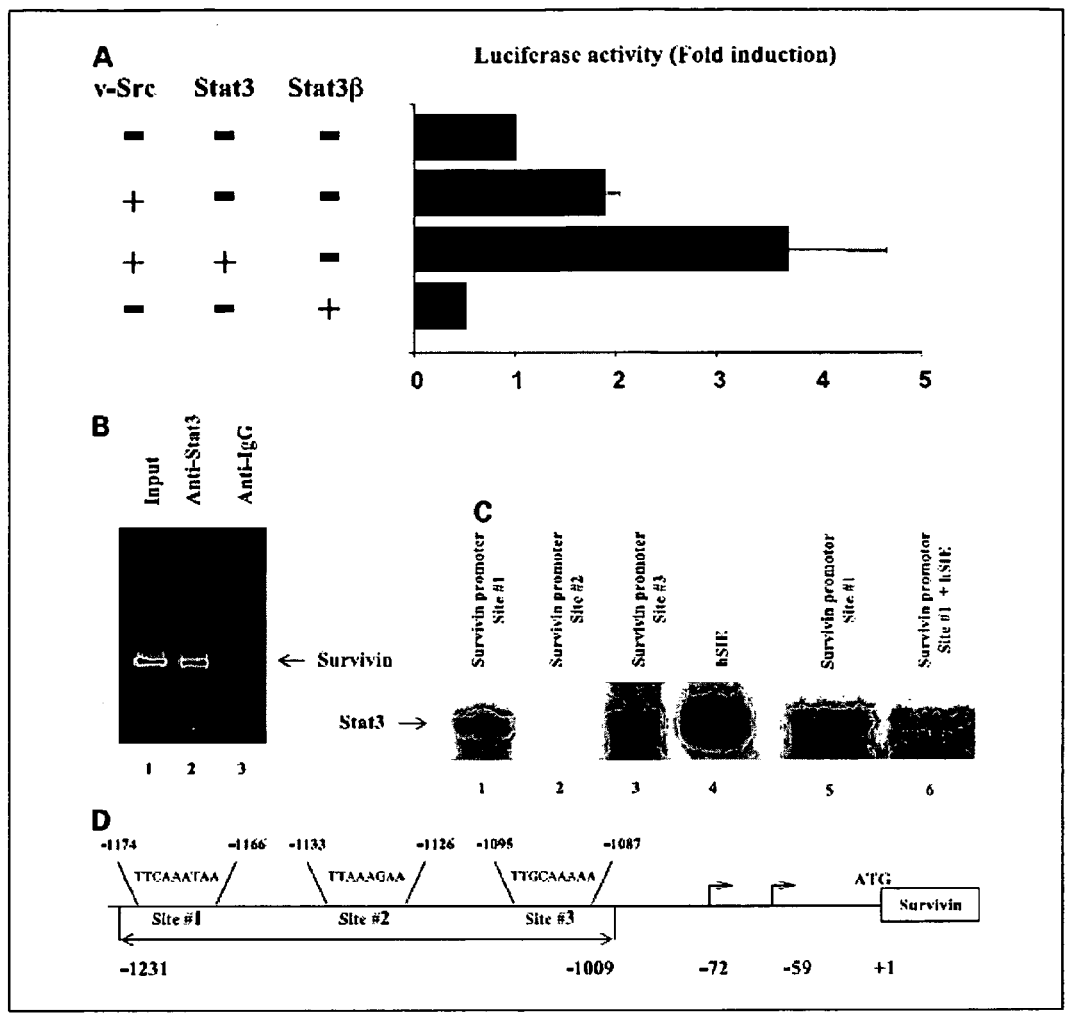
FIG. 4A is a graph of a luciferase assay to monitor activation of the Survivin promoter in response to the indicated treatments.
FIG. 4B is a photograph of a chromatin immunoprecipitation assay demonstrating that Stat3 binds to the Survivin promoter region.
FIG. 4C is a photograph of an EMSA of Stat3 binding activity to the putative Stat3 binding sites in the Survivin promoter region.
FIG. 4D is a schematic view of the Survivin promoter showing the putative Stat3 binding sites.

Cotransfection of the Survivin reporter construct with a v-Src vector that activates endogenous cellular Stat3 induced expression of the Survivin reporter by 2-fold (FIG. 4A). Moreover, cotransfection with both v-Src and full-length Stat3 vectors further induced the Survivin reporter expression up to nearly 5-fold. By contrast, ectopic expression of the dominant-negative Stat3 variant, Stat3β, decreased basal levels of Survivin reporter expression by 50% (FIG. 4A).

A search for potential Stat3-binding sites within the Survivin promoter region revealed five candidates with the consensus sequences $TT(N_4)AA$ (SEQ ID NO: 5) and $TT(N_5)AA$ (SEQ ID NO: 6). The Survivin promoter was described by Li and Altieri, Biochem J 344:305-11 (1999) and the STAT DNA binding sequence was described by Seidel et al., Proc Natl Acad Sci USA 92:3041-45 (1995), both of which are incorporated herein by reference. To determine whether Stat3 could bind the Survivin promoter under physiologic conditions in intact cells, chromatin immunoprecipitation assays were performed using three sets of primers that cover the five candidate Stat3-binding sites. Chromatin immunoprecipitation assays were done as previously described by Wells et al., Mol Cell Biol 20:5797-807 (2000), which is incorporated herein by reference. Briefly, asynchrononously growing HEK-293 cells were incubated with formaldehyde to cross-link protein-DNA complexes. The cross-linked chromatin was then extracted, diluted with lysis buffer, and sheared by sonication. After preclearing with 1:2 mix of protein A/protein G-agarose beads (Life Technologies, Grand Island, N.Y.), the chromatin was divided into equal samples for immunoprecipitation with either anti-Stat3 or anti-immunoglobulin G (negative control) polyclonal antibody (Santa Cruz Biotechnology, Santa Cruz, Calif.). The immunoprecipitates were pelleted by centrifugation and incubated at 56° C. to reverse the protein-DNA cross-linking. The DNA was extracted from the eluate by the phenol/chloroform method and then precipitated by ethanol. Purified DNA was subjected to PCR with primers specific for a region (−1,231 to −1,009) in the human Survivin promoter spanning three putative Stat3-binding sites. The sequences of the PCR primers used are as follows: Survivin forward primer, 5'-CAGTGAGCT-GAGATCATGCC-3' (SEQ ID NO: 7); Survivin reverse primer, 5'-TATTAGCCCTCCAGCCCCCAC-3' (SEQ ID NO: 8).

Primers to the region of −1,231 to −1,009 upstream from the ATG translation initiation site yielded Survivin promoter DNA in chromatin immunoprecipitated with an anti-Stat3 antibody (FIG. 4B). This region contains three potential Stat3 binding sites (FIG. 4D). By contrast, primers to the region of −358/−148 and −938/−759 in the Survivin promoter did not detect promoter DNA in the anti-Stat3 immunoprecipitates.

EMSA was done to determine binding of Stat3 to the same Survivin promoter region in vitro. The oligonucleotides containing the putative Stat3-binding sites in the Survivin promoter used in EMSA are as follows (sense strand): (−1,184) site #1,5'-TGGAGACTCAGTTTCAAATAAATAAATAAAC-3' (SEQ ID NO: 9); (−1,143) site #2,5'-TGAGTTACTGTATTAAAGAATGGGGGCGGG-3' (SEQ ID NO: 10); and (−1,105) site #3,5'-TGTGGGGAGAGGTTGCAAAAATAAATAAAT-3' (SEQ ID NO: 11) (the bolded and underlined oligonucleotides, TG, are sequences added to the 5' end to create overhangs for radiolabeling by Klenow reaction and are not part of the Survivin promoter). Competition analysis to determine specificity of Stat3 binding to the Survivin promoter was done by preincubating unlabeled hSIE probe with radiolabeled Survivin probe in the EMSA. Following incubation of radiolabeled probes with nuclear extracts, protein-DNA complexes were resolved by nondenaturing PAGE and detected by autoradiography.

Results showed that endogenous activated Stat3 protein, present in nuclear extracts of MDA-MB-435s breast cancer cells, bound to the Survivin promoter fragments −1,174/−1,166 (site #1) and −1,095/−1,087 (site #3) but not to fragments −1,133/−1,126 (site #2), −851/−844 (site #4), and −264/−256 (site #5; FIG. 4C and data not shown). Specificity of Stat3 binding to the Survivin promoter fragments #1 and #3 was shown by competition analysis with unlabeled hSIE probe (FIG. 4C and data not shown). Both site #1 and site #3 are located within the −1,231 to −1,009 region that was detected in the chromatin immunoprecipitation assays above with anti-Stat3 antibody, suggesting it is this region of the Survivin promoter that accounts for Stat3 binding. Taken together, these data provide evidence that Stat3 directly binds the Survivin promoter and induces its expression.

Example 5

Stat3 Activation Correlates with Expression of Survivin in Breast Cancer Cells

To investigate whether Stat3 activation correlates with Survivin up-regulation, Western blot analyses for Survivin were completed in a panel of human breast cancer cells harboring constitutively active Stat3 and in normal breast epithelial cells. The Western blots were completed as described above and were probed with polyclonal anti-Survivin antibodies (Alpha Diagnostics International, San Antonio, Tex.). The expression of β-actin (Sigma-Aldrich, St. Louis, Mo.) was used as a normalization control for protein loading. MDA-MB-435s, MDA-MB-468, MDA-MB-231, MDA-MB-361, HEK-293, and NIH 3T3 cells were grown in DMEM supplemented with 10% fetal bovine serum, 100 units/mL penicillin, and 100 μg/mL streptomycin. MCF10A cells were cultured in 1:1 mixture of Ham's F12 medium/DMEM with 2.5 mmol/L L-glutamine and supplemented with 20 ng/mL epidermal growth factor, 100 ng/mL cholera toxin, 0.01 mg/mL insulin and 500 ng/mL hydrocortisone, 5% horse serum, 100 units/mL penicillin, and 100 μg/mL streptomycin.

Figure 5:
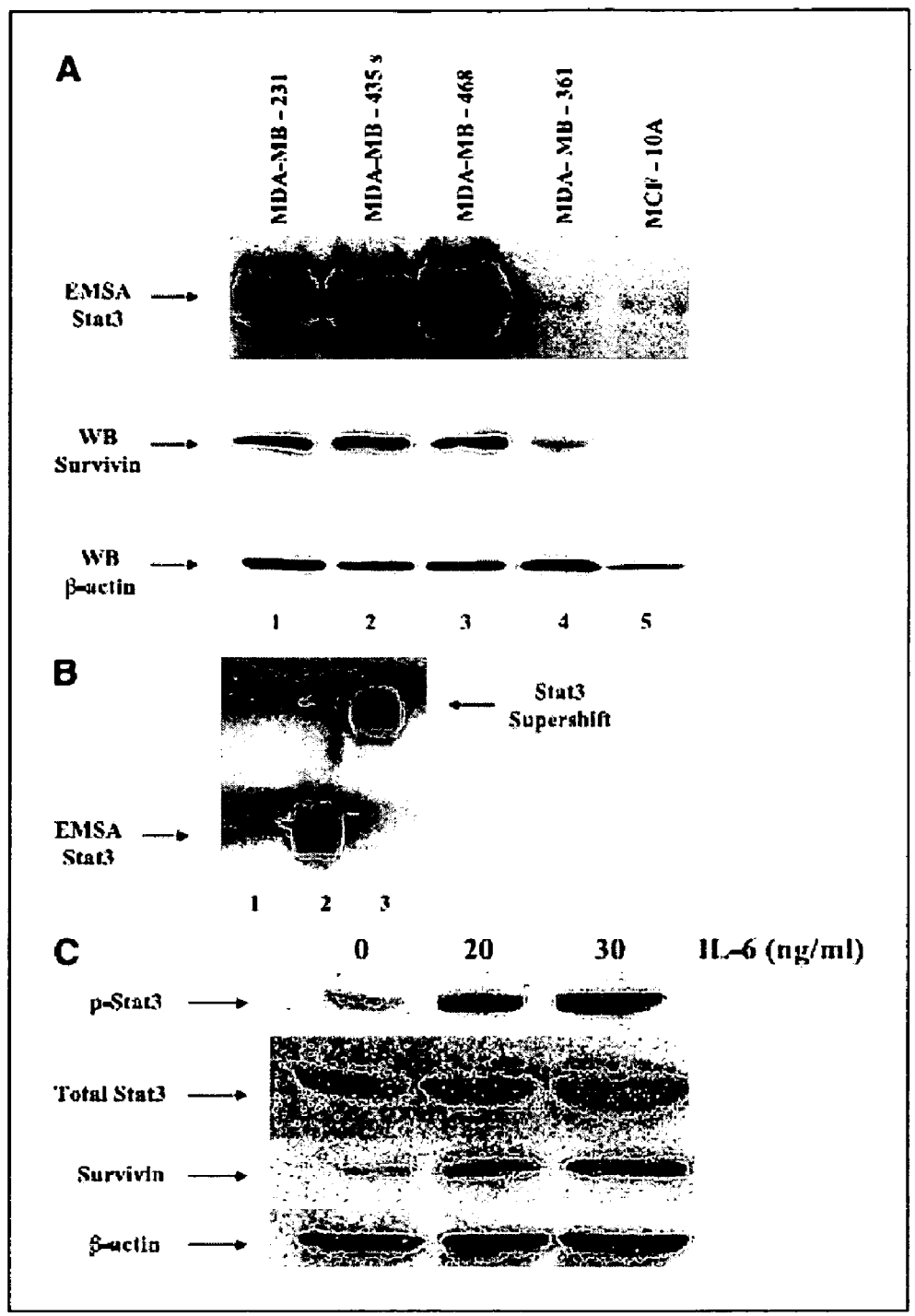
FIG. 5A is a set of photographs of an EMSA for Stat3, and a Western blot for Survivin and Actin in several breast cancer cell lines.
FIG. 5B is a photograph of an EMSA analysis of Stat3 demonstrating a supershift after IL-6 induction.
FIG. 5C is a photograph of a Western blot analysis demonstrating induction of phosphorylated Stat3 and increases in Survivin expression after treatment with IL-6.

Western blot analysis showed Survivin protein expression in all tested breast cancer cell lines with activated Stat3 (MDA-MB-231, MDA-MB-435s, and MDA-MB-468; FIG. 5A). By contrast, minimal Survivin expression was observed in breast cancer cells (MDA-MB-361) and in normal breast epithelial cells (MCF-10A) lacking detectable Stat3 activation. Stat3 activation in each cell line was confirmed by EMSA as described above and shown in FIG. 5A.

To investigate whether cytokine-induced Stat3 activity correlates with increased Survivin expression in breast cancer cells, cells were stimulated with IL-6 to increase Stat3 activation. For IL-6 stimulation, cells were serum-starved (DMEM supplemented with 0.1% fetal bovine serum) for 18 hours before IL-6 treatment (20 or 30 ng/mL in DMEM) for 30 minutes (EMSA) or 48 hours (Western blot analysis). Nuclear extracts and cell lysates were prepared for EMSA and Western blot analysis, respectively, as described above.

IL-6 treatment of serum-starved MDA-MB-435s cells increases Stat3 DNA-binding activity within 30 minutes as detected by EMSA (FIG. 5B). In addition, both phosphor-Stat3 levels and Survivin protein expression were induced by IL-6 treatment of MDA-MB-435s cells after 48 hours (FIG. 5C). These findings indicate that constitutive and cytokine-induced Stat3 activation correlates with Survivin expression in breast cancer cell lines.

Example 6

Immunohistochemical Analysis Comparing Tumor and Nonneoplastic Tissues

Clinical trials and biomarkers. Forty-five women with stage III breast carcinoma were enrolled in a 3-year clinical trial of neoadjuvant dose-dense chemotherapy with sequential doxorubicin (80 mg/m$^2$) followed by docetaxel (100 mg/m$^2$) i.v. every 2 weeks for three cycles each. After neoadjuvant chemotherapy, all participants underwent surgery with either lumpectomy or mastectomy and axillary lymph node dissection. All tumors were at least 5 cm in size, 85% were ductal, 10% were lobular, and 5% had ductal and lobular features. Levels of activated tyrosine-phosphorylated Stat3 (pY-Stat3) and nine other proteins were quantified for their reported relevance to Stat activation or breast oncogenesis: pY-Src, HER2/neu, estrogen receptor (ER), progesterone receptor (PR), Ki-67, Bcl-2, Bcl-x$_L$, epidermal growth factor receptor (EGFR), and Survivin.

Apoptosis in tissues was measured by the terminal deoxynucleotidyl transferase-mediated nick end labeling (TUNEL) assay as described above. In an attempt to identify expression patterns that correlate with response to treatment, the analysis was done in tissues obtained before and after therapy. Before treatment, tissue was obtained by incisional biopsies of tumor and nontumoral parenchyma, either from a distant ipsilateral quadrant or from the contralateral breast (majority of cases). After chemotherapy, tissue was obtained at the time of definitive surgery.

Tissue collection. To preserve the activated phosphorylation state of signal transduction proteins, tissues have to be snap frozen in liquid nitrogen within 15 minutes from the moment of interruption of blood supply to the specimen. All tissues in this study were snap frozen or fixed in 10% neutral-buffered formalin within 15 minutes to minimize antigen loss and optimize immunohistochemical detection. The presence of normal tissue or tumor was confirmed in mirror image sections of the respective samples by examination of frozen sections immediately following collection. After chemotherapy, tumor was only available from those patients with a partial pathologic response. All data obtained were entered into a web-based database for statistical correction of clinical, pathologic, and molecular data.

Heterogeneity of signal across tissue sections. An important aspect of the initial experimentation process was to determine the degree of staining variability across consecutive tissue sections. Twenty consecutive sections were prepared without discarding intervening tissue and used to perform immunohistochemistry for a signaling protein not related to the project (transforming growth factor receptor type II). Quantitative image analysis revealed minimal variation in expression intensity for the first 12 consecutive sections. Expression levels on the next set of 12 sections showed statistically significant differences when compared with the first set. Therefore, a maximum of 11 consecutive sections were used. See Diaz et al., Clin. Cancer Res. 12:20-28 (2006) which is incorporated herein by reference.

Immunohistochemistry and TUNEL procedures. Consecutive 3 μm sections were prepared without discarding intervening tissue (see above). The first section was stained with H&E and the rest of the sections were used for immunohistochemistry and TUNEL assays. For all antigens, except pY-Stat3 (see procedure for pY-Stat3 detection below), the following procedure was used. Formalin-fixed, paraffin-embedded tissue sections were dried at 37° C. overnight. Sections were deparaffinized by an initial warming to 60° C., followed by two xylene changes 10 minutes each, two series of 30 dips in absolute alcohol, 30 dips in 95% alcohol, and 20 dips in deionized water. Antigen retrieval or enzyme digestion procedures were done as described by the supplier of each antibody. Slides were placed for 5 minutes in TBS/Tween and processed on a DAKO Autostainer using the Dako LSAB+ peroxidase detection kit (DAKO, Carpinteria, Calif.). Endogenous peroxide was blocked with 3% aqueous hydrogen peroxide followed by two 20 dips in deionized water.

The anti-EGFR monoclonal antibody clone 111.6 (Signet Pathology Systems, Dedham, Mass.) was applied at 1:100 for 30 minutes following proteinase K digestion (25 μg/mL in TBS/Tween) for 17 minutes. The rest of the antibodies were applied for 30 minutes after microwave antigen retrieval with 0.1 mol/L citrate buffer (pH 6.0; Emerson 1,100 W microwave, high to boiling, then 20 minutes on power level 5) as follows: Bcl-2 (1:40; DAKO), Bcl-x$_L$ (1:50; Santa Cruz Biotechnology, Santa Cruz, Calif.); pY-Src (1:100; Cell Signaling Technology, Beverly, Mass.), Ki-67 (1:50; Immunotech, Norcross, Ga.), c-ErbB-2 (1:40; HER2/neu; Signet Pathology Systems), ER and PR (1:40; BioGenex, San Ramon, Calif.), and Survivin (1:100; Cell Signaling Technology, Beverly, Mass.). The chromogen 3,3'-diaminobenzidine was used for all proteins except for Survivin, which was detected using Nova-Red (Vector Laboratories, Burlingame, Calif.). Survivin expression was evaluated only in samples obtained before treatment because analysis of this antigen was added at later time in this study based on microarray analyses (see above). Counterstain was done with modified Mayer's hematoxylin (Signet Laboratories, Dedham, Mass.). Slides were dehydrated through graded alcohol, cleared with xylene, and mounted with resinous mounting medium. Apoptosis was detected by the TUNEL assay using the Intergen Apopta G Peroxidase In situ Apoptosis detection kit (Intergen, Purchase, N.Y.) as indicated by the supplier.

pY-Stat3 immunohistochemistry. After deparaffinizing, a two-stage pretreatment procedure was done as follows. First, antigen retrieval was done in a pressure cooker by placing a total of 600 ml deionized water in three containers, one containing the slides in citrate buffer (pH 6.0) and the other two containing only deionized water. The microwave oven (Emerson 1, 100 W) was set on high to pressurize for 12 minutes and then at power level 4 for 10 minutes. Slides were then cooled at room temperature for 30 minutes. This was followed by limited enzymatic digestion at 37° C. for 5 minutes with 0.025% trypsin in 5 mmol/L Tris-Cl (pH 7.6) with 0.05% calcium chloride. At the end of the digestion, slides were rinsed with deionized water, placed in TBS/Tween for 5 minutes, drained, and framed with an ImmunoEdge pen. Hydrogen peroxide 3% was applied for 10 minutes and 3% bovine serum albumin/PBS for 10 minutes. Sections were incubated with antiphospho-Stat3 antibody (rabbit polyclonal P-State3, Cell Signaling Technologies, Beverly, Mass.) at 1:400 in a humid chamber at 4° C. overnight and returned to the autostainer for detection and substrate development using the Dako LSAB+ detection system and 3,3'-diaminobenzidine as chromogen. Counterstaining was done for 30 seconds with modified Mayer's hematoxylin. Sections were allowed to sit in tap water for 10 to 15 minutes and dehydrated before mounting with resinous mounting medium.

Image Analysis and quantification. The Optimas 6.5 (Media Cybernetics, Silver Springs, Md.) software was used to quantify protein expression. Regions of interest were identified on the H&E-stained slide and the same areas were marked on the consecutive sections used for each of the biomarkers and TUNEL assay. Digital images of these areas were obtained using identical magnifications (×400) and camera settings with a Leica DM microscope (Leica Microscopes, Bannockburn, Ill.) with neutral density 6 and 12 filters, coupled to a SPOT Digital Camera System (Diagnostic Instruments, Sterling Heights, Mich.) and SPOT software set as AutoGain, RGB filter color, non binning, full chip area, and adjustment factor set to 1. Before photography, Koehler epi-illumination was done. Optimal light conditions for each objective were stored as software settings to be replicated in each measurement session. Image acquisition was done after 1 hour of microscope lamp warm up. White balance was done on an area of the slide with no tissue, and background values were subtracted using a negative control slide. Images of the selected areas were stored as TIFF images. A macro was specifically set in the software to automate the process and transfer mathematical calculations to a Microsoft Excel spreadsheet. These were converted to SAS data sets for statistical analysis. Quantitative image analysis was done on all pretreatment samples and in those posttreatment samples for which tumor tissue was still identifiable (partial pathologic responders).

Figure 6:
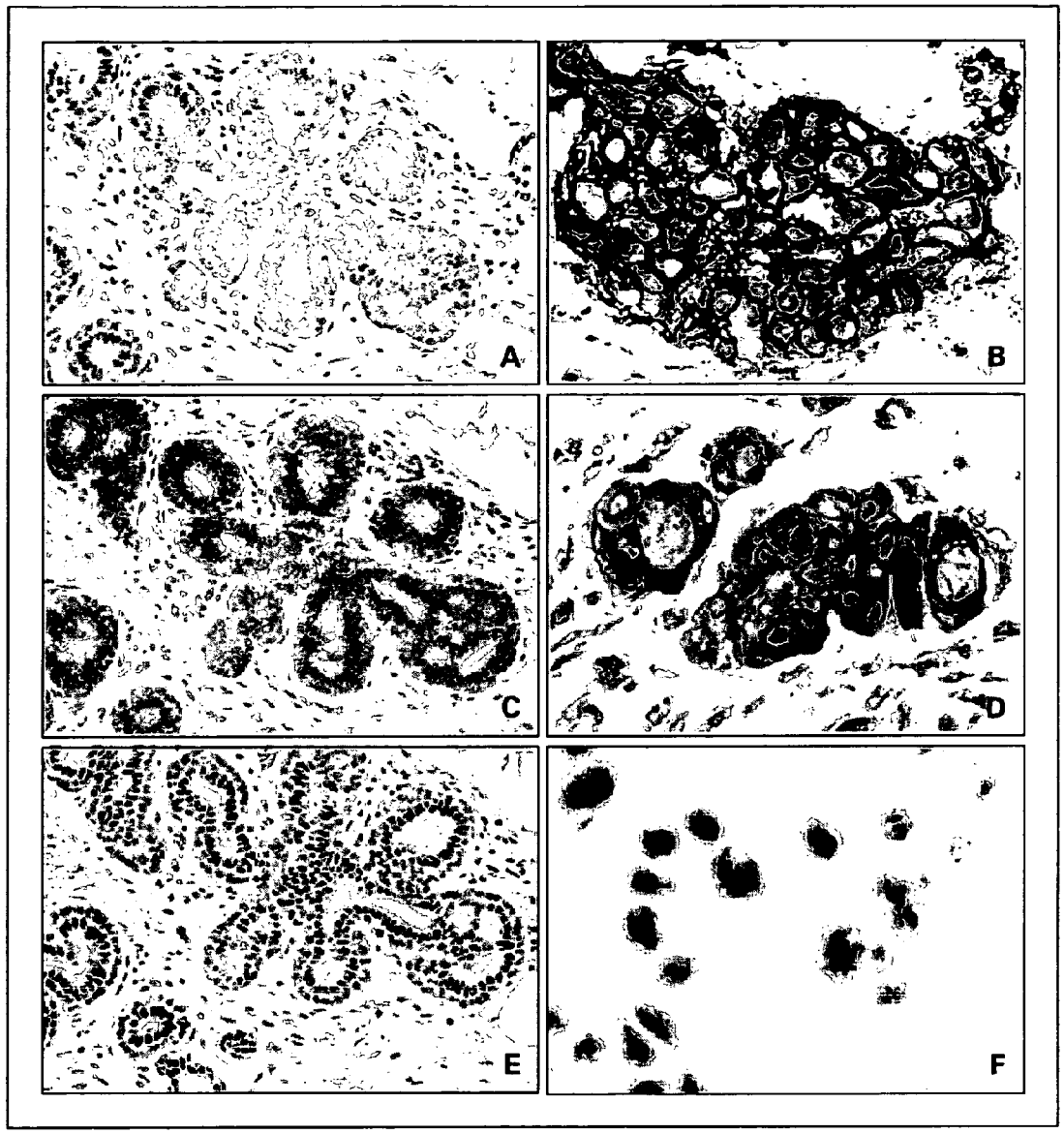
FIG. 6 is a set of photographs showing immunohistochemical staining for HER2/neu (A and B), pY-Src (C and D) and pY-Stat3 (E and F) on nonneoplastic tissue (A, C, and E) and paired carcinoma (B, D, and F).

Immunohistochemistry and quantitative image analysis. FIG. 6 shows examples of immunohistochemical staining in serial sections of nontumor (A, C, and E) and matched tumor tissues (B, D, and F) from the same patient using antibodies to HER2/neu (A and B), pY-Src (C and D), and pY-Stat3 (E and F). For quantification by digital image analysis, regions of interest were selected to include only epithelial components (nonneoplastic or carcinoma) and to eliminate mesenchymal areas. Each of the markers was evaluated in its corresponding cellular compartment (nucleus, cytoplasm, or membrane). In the case of predominantly nuclear markers like pY-Stat3 (A, B, and C), thresholds were set to discriminate between the brown color of 3,3'-diaminobenzidine (or the red color of Nova-Red for Survivin) and the blue color of hematoxylin in negative nuclei. For membranous markers like HER2/neu (D, E, and F), the 3,3'-diaminobenzidine signal was measured as a percentage of the total cellular area after subtraction from the region of interest of both nuclear and cytoplasmic components. For predominantly cytoplasmic markers like pY-Src (G, H, and I), the brown 3,3'-diaminobenzidine signal was quantified in the total cellular area of the selected region of interest after subtraction of the blue nuclear area. In all three situations, positive signals were reported as an index reflecting the optical intensity of the marker in relationship to the total optical intensity of the region of interest (average of three measurements).

HER2/neu clinical testing. HER/2neu status was also assessed in all tumors at an independent laboratory using a Food and Drug Administration-approved immunohistochemistry procedure. Results of this test are reported negative when intensity scores are 0 or 1+ and positive when the intensity score is 3+. Cases with intermediate intensity score of 2+ are further evaluated by fluorescence in situ hybridization. Using this method, 11 cases (24.4%) were positive, 31 (68.9%) were negative, and 3 (6.7%) remained undetermined. These percentages are consistent with previous reports. In the group of tumors that were positive by the Food and Drug Administrative-approved test, the average HER2/neu index calculated by computerized image analysis in this study was 50 and the SD 14.5. In the group of tumors that were negative by the Food and Drug Administrative-approved test, the average HER2/neu index by computerized image analysis was 35.5 and the SD was 30. The difference was not statistically significant but suggested a similar trend of HER2/neu detection with both methods.

Statistical considerations. Before statistical evaluation, pathologic response was classified as either complete pathologic response (CPR) or partial pathologic response (PPR) based on the size of residual tumor after treatment (complete pathologic response if 0 cm, partial pathologic responses if >0 cm). Biomarker values were analyzed by descriptive statistics, including mean, SD, and range (minimal-maximal), values in all patients as a group and in the complete pathologic response and partial pathologic response groups separately both in nonneoplastic tissue and in tumor tissue. Comparison of pretreatment samples between the complete pathologic response and partial pathologic response groups was examined using the Student's t test if the data followed a normal distribution and the Wilcoxon Mann-Whitney test if the normality assumption was not met. In addition, pretreatment to posttreatment changes were evaluated using the paired t test in the partial pathologic response group. Correlations between pretreatment values were assessed by the Spearman's rank correlation coefficient. No adjustments were made for multiple testing owing to the exploratory nature of this study. All tests were two-sided and declared significant at the 5% level.

Table 2 summarizes the descriptive statistics of the immunohistochemical quantitative analysis in nonneoplastic and tumor tissues by pathologic response for pretreatment and posttreatment. Of the 45 patients included in the clinical trial, 12 (27%) showed a complete pathologic response and 33 (73%) showed a partial pathologic response. Statistical analysis of the immunohistochemical data was done in all 45 patients as a group and in the complete pathologic response and partial pathologic response groups separate, as described below.

TABLE 2

Descriptive statistics of molecular biomarker values as measured by immunohistochemistry in non-neoplastic tissues (N) and tumors (T)

|  | Pretreatment ALL | | Pretreatment CPR | | Pretreatment PPR | | Posttreatment PPR | |
| --- | --- | --- | --- | --- | --- | --- | --- | --- |
|  | N | T | N | T | N | T | N | T |
| Bcl-2 | 45.4 | 21.7 | 47.3 (31.1) | 18.4 (16.5) | 44.8 (25.4) | 22.9 (19.8) | 55.4 (27.6) | 35.5 (23.7) |
|  | (26.7) | (18.9) | [3.2-97.8] | [0.6-47.1] | [1.2-97.8] | [0-83.6] | [8.8-96.2] | [0.3-87.2] |
| Bcl-xL | 43.8 | 35.5 | 50.1 (13.6) | 37.7 (28.4) | 41.5 (22.3) | 34.8 (27.3) | 42.4 (25.6) | 39.9 (30.4) |
|  | (20.5) | (27.3) | [39.9-65.5] | [0.1-7.3] | [1.4-71.2] | [0.7-99.8] | [0.1-92] | [0.9-95.4] |
| EGFR | 28.1 | 27.7 | 19.4 (16.0) | 29.6 (26.1) | 31.3 (27.0) | 27.1 (25.3) | 30.3 (22.5) | 35.5 (26.6) |
|  | (25.0) | (25.3) | [0.7-45.2] | [0.1-76.1] | [0.1-95.3] | [0.1-98.7] | [0.4-81.1] | [0.9-782] |
| ER | 35.6 | 24.9 | 35.1 (24.6) | 22.9 (20.0) | 35.8 (27.2) | 25.6 (29.2) | 42.3 (25.1) | 31.2 (25.1) |
|  | (26.3) | (26.8) | [1.7-79.2] | [0.8-65] | [0.9-91.2] | [0-98] | [0.1-93.4] | [0-84.2] |
| PR | 36.4 | 40.3 | 36.9 (26.7) | 46.2 (35.9) | 36.2 (27.0) | 38.2 (33.3) | 32.5 (21.3) | 37.0 (26.7) |
|  | (26.6) | (33.8) | [3.9-84.0] | [0-88.1] | [0-89.7] | [0-91.3] | [0-93.4] | [0.9-83.8] |
| Ki-67 | 17.9 | 39.6 | 19.9 (17.0) | 47.6 (28.7) | 17.1 (26.0) | 36.6.(24.0) | 7.1 (11.9) | 24.3 (22.9) |
|  | (23.8) | (25.4) | [0.2-53.3] | [0.9-95.4] | [0-95.2] | [0.9-87.5] | 0.1-42.6] | [0-88.7] |
| pY-Src | 25.7 | 49.0 | 19.5 (24.2) | 58.4 (25.6) | 28.0 (24.4) | 45.5 (28.5) | 31.8 (26.9) | 53.5 (30.2) |
|  | (24.4) | (28.0) | [0.9-77.9] | [0.9-88.5] | [0-95.2] | [0.1-97.7] | [0.5-93.4] | [0.9-98.1] |

TABLE 2-continued

Descriptive statistics of molecular biomarker values as measured by immunohistochemistry in non-neoplastic tissues (N) and tumors (T)

| | Pretreatment ALL | | Pretreatment CPR | | Pretreatment PPR | | Posttreatment PPR | |
|---|---|---|---|---|---|---|---|---|
| | N | T | N | T | N | T | N | T |
| pY-Stat3 | 27.8 (17.3) | 52.1 (26.8) | 22.8 (15.8) [0.8-53.8] | 40.6 (21.0) [0.9-78.4] | 29.7 (17.7) [0.9-89.7] | 56.4 (27.7) [0.9-98.5] | 24.6 (14.4) [0.1-64.8] | 53.6 (25.9) [0.9-92.9] |
| TUNEL | 34.9 (27.0) | 23.9 (24.8) | 43.3 (28.9) [0.9-100] | 22.4 (20.9) [0.9-67.5] | 31.7 (26.0) [0.9-65.8] | 24.5 (26.4) [0.1-76.2] | 30.4 (22.3) [0.9-61.5] | 21.5 (22.8) [0.9-84.3] |
| HER2/neu* | — | 39.1 (27.6) | — | 29.0 (24.4) [0.6-79.6] | — | 42.6 (28.1) [0.1-89.5] | — | 41.6 (22.9) [0.1-89.2] |
| Survivin* | — | 25.8 (24.4) | — | 29.4 (27.6) [1.3-71.3] | — | 23.8 (23.3) [0-76.3] | — | NA |

NOTE:
The analysis was done for all patients as a group (ALL) as well as in the subgroups of complete pathologic responders and partial pathologic responders before and after chemotherapy treatment. All values are expressed as an index with a range between 0 and 100 reflecting relative intensities of staining for each biomarker. Data are means with SD in parentheses for all groups and ranges in brackets for the complete pathologic response and partial pathologic response subgroups only. There was no detectable expression of Survivin or HER2/neu in normal breast epithelium.
Abbreviations: N, non-neoplastic tissues; T, tumors; CPR, complete pathologic responders; PPR, partial pathologic responders; NA, not available.
*No detectable levels of Survivin or HER2/neu were observed in non-neoplastic tissues; NA, not available.

Molecular biomarker levels in tumor versus nonneoplastic tissues. Table 3 shows that in tissues obtained before chemotherapy treatment, levels of pY-Stat3, pY-Src, and Ki-67 were significantly higher in tumors than in nonneoplastic tissues, both when all tumors were analyzed as a group without regard to pathologic response ($P \leq 0.001$) and when the analysis was done in the complete pathologic response and partial pathologic response groups separately. In contrast, pretreatment levels of ER in the complete pathologic response group, and Bcl-2 in both complete pathologic response and partial pathologic response groups, were significantly higher in nonneoplastic tissues than in tumors (compare Tables 2 and 3). Similar relationships were found in tissues after chemotherapy treatment, with higher levels of pY-Stat3, pY-Src, and Ki-67 in tumors and higher levels of Bcl-2 in nonneoplastic tissues.

TABLE 3

Statistical analysis (P values) of differences in biomarker values between tumors and paired nonneoplastic tissues

| | Pretreatment | | | Posttreatment |
|---|---|---|---|---|
| | ALL | CPR | PPR | PPR |
| Bcl-2 | <0.001 | 0.016 | <0.001 | 0.003 |
| Bcl-xL | 0.067 | 0.197 | 0.191 | 0.710 |
| EGFR | 0.950 | 0.255 | 0.552 | 0.394 |
| ER | 0.038 | 0.016 | 0.139 | 0.036 |
| PR | 0.547 | 0.523 | 0.786 | 0.433 |
| Ki-67 | 0.001 | 0.001 | 0.006 | 0.001 |
| pY-Src | <0.001 | 0.001 | 0.003 | 0.003 |
| pY-Stat3 | <0.001 | 0.010 | <0.001 | <0.001 |
| HER2/neu* | — | — | — | — |
| Survivin* | — | — | — | — |
| TUNEL | 0.054 | 0.084 | 0.265 | 0.061 |

NOTE:
Analysis was done in the entire group of patients (ALL) and in the subgroups of complete pathologic responders and partial pathologic responders before and after chemotherapy treatment.
*No detectable levels of Survivin or HER2/neu were observed in non-neoplastic tissues.

Correlation between biomarker levels in tumors. No significant correlations were found among biomarkers in nonneoplastic tissues, either in the pretreatment or in the posttreatment groups (data now shown). In tumors, however, the following significant statistical correlations among molecular biomarkers were observed (Table 4).

TABLE 4

Significant correlations between biomarker values in tumors

| | | r | P |
|---|---|---|---|
| Pretreatment ALL | | | |
| ER | EGFR | 0.27 | 0.015 |
| PR | Bcl-2 | 0.24 | 0.040 |
| | Bcl-$x_L$ | 0.14 | 0.031 |
| pY-Src | Bcl-2 | 0.22 | 0.028 |
| | Bcl-$x_L$ | 0.36 | 0.024 |
| | Ki-67 | 0.39 | 0.016 |
| pY-Stat3 | HER2/neu | 0.37 | 0.017 |
| | Survivin | 0.29 | 0.032 |
| Pretreatment-CPR | | | |
| BCL-2 | Bcl-$x_L$ | 0.65 | 0.020 |
| | PR | 0.69 | 0.007 |
| pY-Stat3 | HER2/neu | 0.54 | 0.048 |
| | pY-Src | 0.66 | 0.028 |
| Survivin | EGFR | 0.72 | 0.088 |
| Pretreatment PPR | | | |
| ER | EGFR | 0.37 | 0.025 |
| pY-Src | Bcl-2 | 0.27 | 0.009 |
| | Bcl-$x_L$ | 0.42 | 0.036 |
| | EGFR | 0.41 | 0.014 |
| pY-Stat3 | ER | 0.41 | 0.050 |
| | Survivin | 0.53 | 0.001 |
| Posttreatment PPR | | | |
| HER2/neu | Ki-67 | 0.39 | 0.024 |
| EGFR | pY-Src | −0.38 | 0.028 |

NOTE:
Spearman's test was used to identify statistically significant correlations among the expression levels of biomarkers in tumors. Only statistically significant correlations ($P \leq 0.05$) are shown, together with the correlation coefficient ®.

Pretreatment. When pretreatment tumors were analyzed as a group, without regard to pathologic response, ER correlated with EGFR; PR with Bcl-2 and Bcl-$x_L$; pY-Src with Bcl-2, Bcl-$x_L$, EGFR, and Ki-67; and pY-Stat3 with HER2/neu and Survivin. In the complete pathologic response group, Bcl-2 correlated with Bcl-$x_L$ and PR, and pY-Stat3 with HER2/neu and pY-Src. In the partial pathologic response group, EGFR correlated with ER and TUNEL; pY-Src with Bcl-2, Bcl-$x_L$ and PR, and EGFR; and pY-Stat3 with ER and Survivin. When pretreatment tumor values in the complete pathologic response group were compared with those of the partial pathologic response, only pY-Stat3 was found to have a statistically significant correlation with response to therapy (P=0.028). Levels of pY-Stat3 were lower in tumors of patients who showed complete pathologic response, suggesting that higher levels of activated Stat3 made tumors less responsive to the treatment. Taking all of the data into consideration, the most statistically significant correlation with clinical relevance among the pretreatment biomarkers was between pY-Stat3 and Survivin levels in the partial pathologic response group (P=0.001).

Posttreatment. In the posttreatment partial pathologic response group, a direct correlation between HER2/neu and Ki-67 and an inverse correlation between EGFR and pY-Src were observed.

Pretreatment versus posttreatment (partial pathologic responders only). Levels of Ki-67 were higher in pretreatment samples than in posttreatment samples (P<0.02), and levels of Bcl-2 were higher in posttreatment samples than in pretreatment samples (P<0.02).

Example 7

Figure 7:
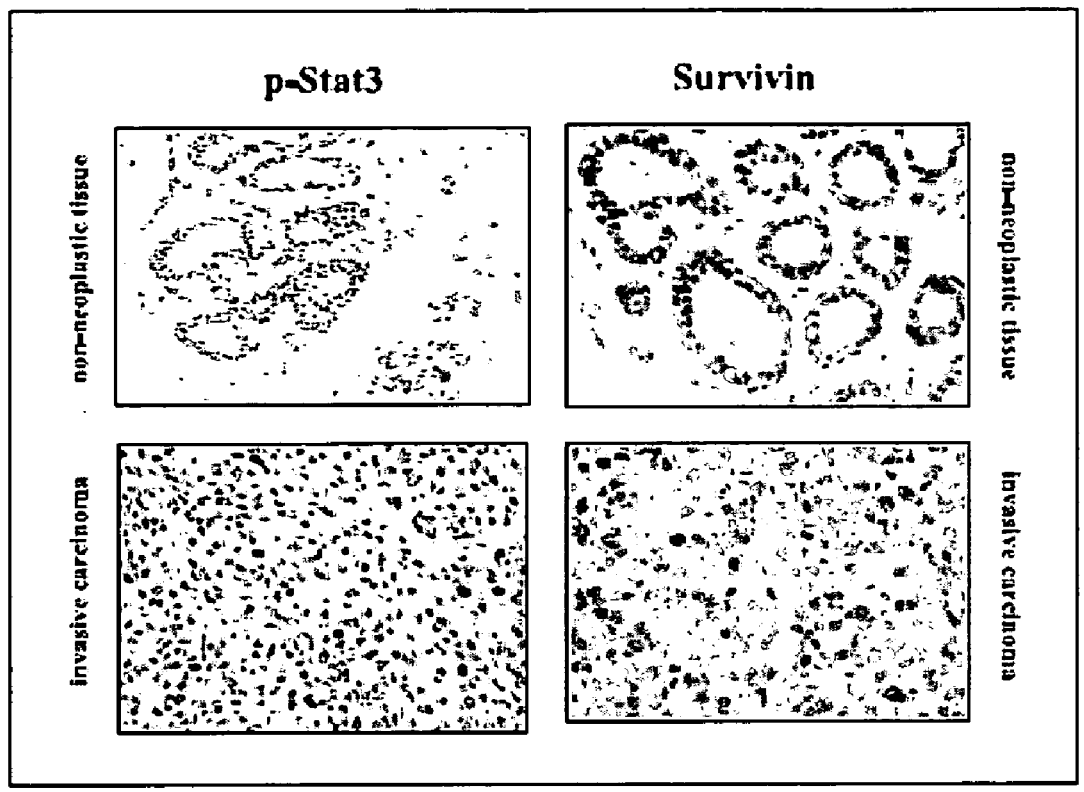
FIG. 7 is a set of photographs showing immunohistochemical staining for phosphor-Stat3 and Survivin in primary breast tumors and non-neoplastic tissue.

Stat3 Activation and Survivin Expression Correlate with Response to Chemotherapy The association between constitutive Stat3 activation and Survivin expression in primary breast tumors was investigated. Tissue specimens were analyzed by immunohistochemical staining of formalin-fixed, paraffin-embedded sections using phosphor-Stat3 or Survivin antibodies. Moderate to strong predominantly nuclear staining was observed for phosphor-Stat3 and Survivin in a majority of the tumor specimens but not in normal breast epithelial cells (FIG. 7). Importantly, a statistically significant positive correlation (P=0.001) was observed between elevated phosphorylated Stat3 levels and Survivin expression in 33 of the 45 breast cancer patients who displayed a partial pathologic response to this neoadjuvant chemotherapy regimen. Thus, high levels of phosphorylated Stat3 and Survivin expression correlate with invasive breast cancer and resistance to chemotherapy.

Correlation of molecular biomarkers with response to chemotherapy. As described above, Stat3 activity was measured by both immunohistochemistry and EMSA in the pretreatment tumor and matched normal tissue samples. The other markers, including phosphorylated-Src, HER2/neu, EGF-R, ER, Ki-67, apoptotic index (TUNEL), Bcl-2, Bcl-$x_L$, and Survivin, were measured by immunohistochemistry. Of all the molecular biomarkers examined, only activated phosphorylated Stat3 measured by immunohistochemistry was statistically associated (p=0.028) with decreased likelihood of pathologic complete response to the chemotherapy. Our statistical analysis estimates that the odds of a pathological complete response decreases by a factor of 0.93 for every unit increase in phosphorylated Stat3 levels (Table 5).

TABLE 5

Molecular Biomarkers that Predict Pathologic Complete Response

| Molecular Biomarker | Estimated Coefficient | Standard Error | P-Value | Odds Ratio | (95% CI) |
|---|---|---|---|---|---|
| p-Stat3 | −0.0704 | 0.0320 | 0.0277 | 0.93 | (0.88-0.99) |
| p-Src | 0.0410 | 0.0241 | 0.0885 | 1.04 | (0.99-1.09) |
| Survivin | 0.0183 | 0.0233 | 0.4301 | 1.02 | (0.97-1.07) |
| Her2/neu | −0.0206 | 0.0206 | 0.3177 | 0.98 | (0.94-1.02) |
| EGF-R | −0.0183 | 0.0210 | 0.3841 | 0.98 | (0.94-1.02) |
| ER | 0.0296 | 0.0290 | 0.3073 | 1.03 | (0.97-1.09) |
| Ki-67 | 0.0263 | 0.0235 | 0.2619 | 1.03 | (0.98-1.08) |
| Tunel | −0.0192 | 0.0217 | 0.3766 | 0.98 | (0.94-1.02) |
| Bcl-2 | −0.0471 | 0.0331 | 0.1550 | 0.95 | (0.89-1.02) |
| Bcl-xL | 0.00700 | 0.0167 | 0.6749 | 1.01 | (0.98-1.04) |

Figure 8:
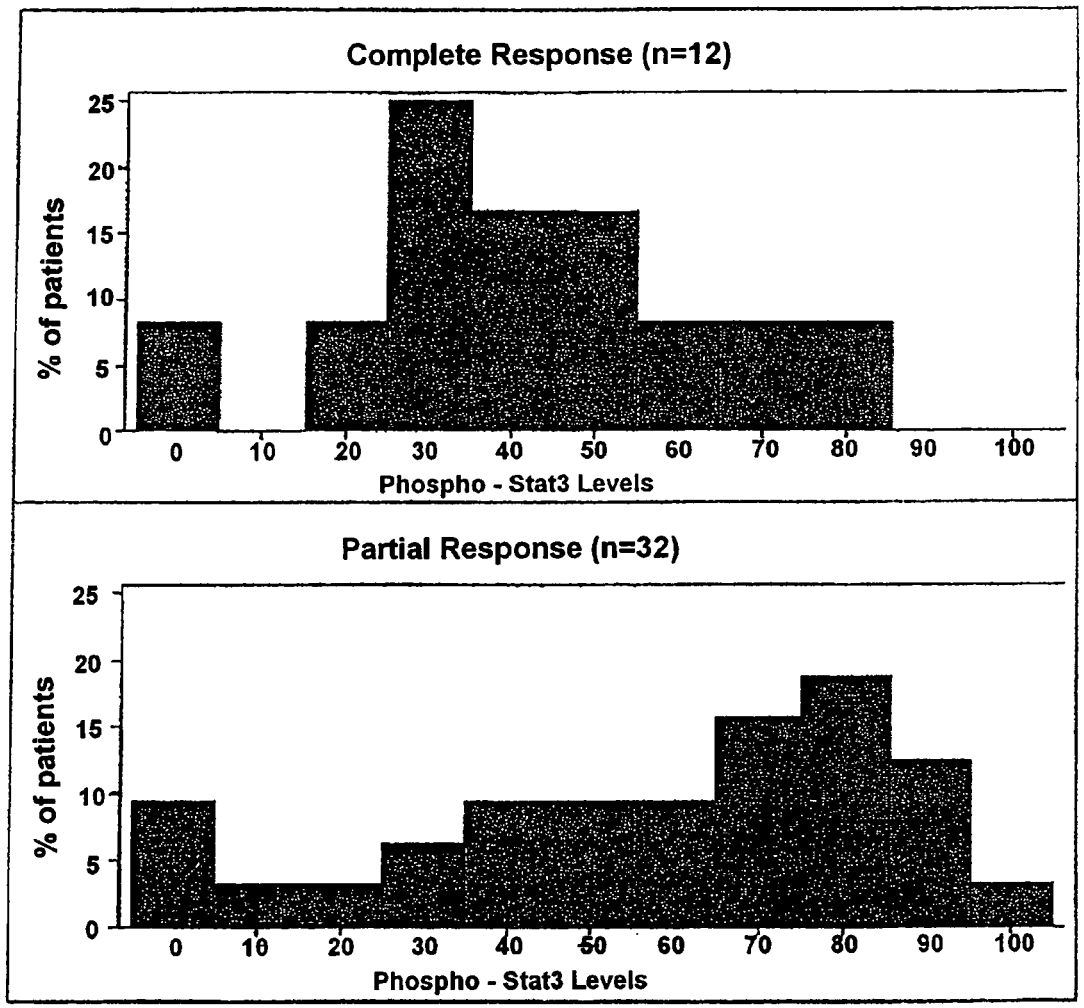
FIG. 8 is a graph demonstrating the relationship between response to neoadjuvant chemotherapy treatment and pre-treatment levels of phosphorylated Stat3.

FIG. 8 illustrates the distribution of phosphorylated Stat3 levels measured by immunohistochemistry in the complete versus partial pathologic response groups. Although statistical comparison of the medians for each of the distributions was marginally significant (p=0.057 by the Wilcoxon rank sum test), examination of the data indicates that the levels of phosphorylated Stat3 tend to be greater in the partial pathological response group.

Example 8

Stat3 Activation in Non-Small Cell Lung Cancer

Tissue arrays and immunohistochemistry. The tissue arrays from stage 1 NSCLC have been described by Zheng et al., Chest 128:308-16 (2005), which is incorporated herein by reference. The samples collected for our tissue microarray construction met the following requirements: (a) diagnosis of stage 1 NSCLC without preoperative radiation or chemotherapy, (b) surgically resected specimens formalin fixed and embedded in paraffin block, and (c) adequate tumor tissue in size for at least three tissue cores. Immunostaining for phosphorylated Stat3 was done as described above using a rabbit anti-human polyclonal antibody (phosphotyrosine-Stat3 705; Cell Signaling Technology, Beverly, Mass.); as negative controls, rabbit immunoglobulins (Vector, Burlingame, Calif.) were used as a primary antibody. Immunostaining for pEGFR was done using a rabbit anti-human polyclonal antibody (phosphotyrosine-EGFR 845, Cell Signaling Technology, Beverly, Mass.).

Immunohistochemical staining of the slides was reviewed and scored. For phosphorylated Stat3, the score system included counting the percentage of nuclear phosphorylated Stat3-stained tumor cells and estimating the intensity of nuclear phosphorylated Stat3-stained tumor cells in a semiquantitative manner. Because transcriptional activity of Stat3 requires nuclear localization to regulate gene expression, we chose nuclear staining instead of cytoplasmic staining. For pEGFR, the score system included counting the percentage of positively stained tumor cells and estimating the intensity staining in a semiquantitative manner. Intensity was classified as 0 to 3 (0=no staining, 1=weak staining, 2=medium, and 3=strong staining). For triplicate samples, mean values of the percentage of staining, the intensity, and a composite score (percentage multiplied by intensity, range 0-300) were derived.

Patterns of activated, phosphorylated Stat3 were characterized using high-density tissue microarrays using surgical resected NSCLC. Primary NSCLC from 176 patients were arrayed in triplicate. A phosphotyrosine 705-Stat3 antibody was used to investigate the levels and cytologic locations of activated Stat3 (termed pStat3) in tumor specimens as described by Mora et al., Cancer Res 62:6659-66 (2002), which is incorporated herein by reference. Tyrosine 705 on Stat3 is phosphorylated by upstream tyrosine kinases, such as EGFR, and this allows for dimer formation, translocation to the nucleus, and DNA binding. Because transcriptional activity of Stat3 requires nuclear localization to regulate gene expression, nuclear staining was evaluated. For each tumor, the mean composite nuclear phosphorylated Stat3 score (intensity multiplied by percentage of tumor cells stained in the three cores) was recorded and correlated with clinical and pathologic variables. A description of the patient characteristics is shown in Table 6.

TABLE 6

Patient demographics

| Patient characteristics | n (%) |
|---|---|
| Total | 176 |
| Age (range) | 45-84 |
| Age (median) | 69 |
| Men | 97 (55.1) |
| Women | 79 (44.9) |
| White | 170 (96.6) |
| Other race | 6 (3.4) |
| Active smoker | 42 (23.9) |
| Former smoker | 92 (52.3) |
| Lifelong nonsmoker | 26 (14.8) |
| Unknown smoking | 16 (9.1) |
| Histology | |
| Adenocarcinoma | 69 (39.2) |
| Bronchioloalveolar carcinoma | 26 (14.8) |
| Squamous | 58 (33.0) |
| Large cell | 23 (13.1) |
| Pathologic stage | |
| IA | 72 (40.9) |
| IB | 94 (53.4) |
| >I | 10 (5.7) |
| Follow-up | |
| Follow-up | 0-146 mo |
| Median follow-up | 37 mo |
| Total alive | 96 (54.5) |
| Total dead | 80 (45.5) |

Abbreviation: pStage, pathologic stage.

Results of phosphorylated Stat3 staining and correlations with patient characteristics are shown in Table 7.

TABLE 7

Correlation of pStat3 with patient characteristics

| | pStat3 positive | pStat3 negative | Percentage pStat 3 positive |
|---|---|---|---|
| Age | | | |
| P | 0.20 | | |
| Sex | | | |
| Male | 49 | 48 | 51% |
| Female | 45 | 34 | 57% |
| P | 0.27 | | |
| Tumor size | | | |
| P | <0.0001 | | |
| Stage | | | |
| IA | 44 | 28 | 61% |
| IB | 44 | 50 | 47% |
| P | 0.11 | | |
| Pack-year smoking | | | |
| P | 0.02 | | |
| Histology | | | |
| Adeno/BAC | 58 | 37 | 61% |
| Large | 11 | 12 | 48% |

TABLE 7-continued

Correlation of pStat3 with patient characteristics

| | pStat3 positive | pStat3 negative | Percentage pStat 3 positive |
|---|---|---|---|
| Squamous | 25 | 33 | 43% |
| P | 0.09 | | |

NOTE:
Percentages of pStat3-positive and pStat3-negative patients are shown based on sex, stage, and histology.
Abbreviations: Adeno, adenocarcinoma; BAC, bronchioloalveolar carcinoma.

These results show nuclear pStat3 expression in 54% of tumors (composite score range 0-222). Higher pStat3 expression was found in patients with limited smoking history (P=0.02) and in smaller tumors (P<0.0001). A trend toward higher pStat3 expression was identified in tumors with bronchioloalveolar carcinoma or adenocarcinoma histology compared with either squamous cell or large cell histology (P=0.09). No relationship was identified between pStat3 and either overall or disease-free survival following surgical resection.

These results are similar to those reported earlier for pEGFR. As reported by Zheng et al., Chest 128:308-16 (2005), expression of pEGFR was noted in 51% of tumor tissues with higher expression in patients with low smoking history and in smaller tumors. Consistent with laboratory studies showing EGFR signaling can activate Stat3, a very strong correlation was identified between pEGFR expression and pStat3 expression in this patient cohort (Spearman's p=0.55, P<0.0001).

Example 9

Stat3 Activation Promotes Tumor Survival

Phosphorylated Stat3 expression was next correlated with apoptosis within the primary tumor. Tumor apoptosis was evaluated by detecting apoptotic cells and apoptotic bodies using in situ labeling with an ApopTag Plus Peroxidase In situ Apoptosis Detection kit (Chemicon International, Temecula, Calif.). This technique detects DNA fragmentation due to apoptosis at the single cell level. The 3'-OH termini generated by DNA end nicking were labeled with modified nucleotides by terminal deoxynucleotidyl transferase, which more selectively detects apoptotic cells rather than necrotic cells. The incorporation of these modified nucleotides was assayed by a specific antibody in immunohistochemical analysis. The scoring system for ApopTag involved counting the percentage of positively stained tumor cells, estimating the intensity staining of a semiquantitative manner as before, generating a composite score and taking the mean value from the three cores. Consistent with the role of Stat3 in promoting tumor cell survival, a negative correlation between phosphorylated Stat3 and tumor apoptosis was found (Spearman's p=−0.19, P=0.01). This result is consistent with less apoptosis in tumors having higher amounts of phosphorylated Stat3.

Example 10

Stat3 Activation Correlates with Sensitivity to EGFR Inhibitors

Cell lines and cell culture. Human NSCLC cell lines were purchased from American Type Culture Collection (ATCC; Manassas, Va.). H3244 cells were provided by Dr. Pasi Janne and grown as described in Fujishita et al., Oncology 64:399-

406 (2003), which is incorporated herein by reference. All other cells were grown in RPMI 1640 supplemented with 2 mmol/L L-glutamine (Santa Cruz Biotechnology, Santa Cruz, Calif.) and 5% bovine calf serum (Hyclone). Subconfluent cells were prepared for protein extracts as detailed below. Cell numbers were determined by counting with a hemocytometer. Gefitinib (ZD1839) was provided by Astra Zeneca (Wilmington, Del.).

Cytotoxicity assays. Cytotoxicity assays [3-(4,5-dimethylthiazol-2-yl)-2,5-diphenyltetrazolium bromide] were done according to the recommendations of the manufacturer (Roche, Indianapolis, Ind.). Cells were counted and $5 \times 10^4$ cells were placed into single wells in a 96-well plate. Cells were grown as above and exposed to the indicated agents as described. Cell viability was assessed following 72 hours. Data presented represents two separate experiments with eight data points per condition. Data were expressed as mean of eight data points.

Protein expression analysis. Cell lysates were normalized for total protein content (50 μg) and subjected to SDS-PAGE as described by Song et al., Oncogene 22:4150-65 (2003). Primary antibodies used in these studies consisted of Stat3 (Transduction Laboratories; BD Biosciences, Mississauga, Ontario, Canada), pStat3 Y705 (Cell Signaling Technology), cleaved poly (ADP-ribose) polymerase (Cell Signaling Technology, Beverly, Mass.), Mcl-1 (Santa Cruz Biotechnology, Santa Cruz, Calif.), Bcl-2 (DAKO, Carpinteria, Calif.), Bcl-xL (PharMingen, San Diego, Calif.), and β-actin (Sigma-Aldrich, Milwaukee, Wis.). Detection of proteins was accomplished using horseradish peroxidase-conjugated secondary antibodies and enhanced chemiluminescence purchased through Amersham Biosciences (Pittsburgh, Pa.).

Figure 9:
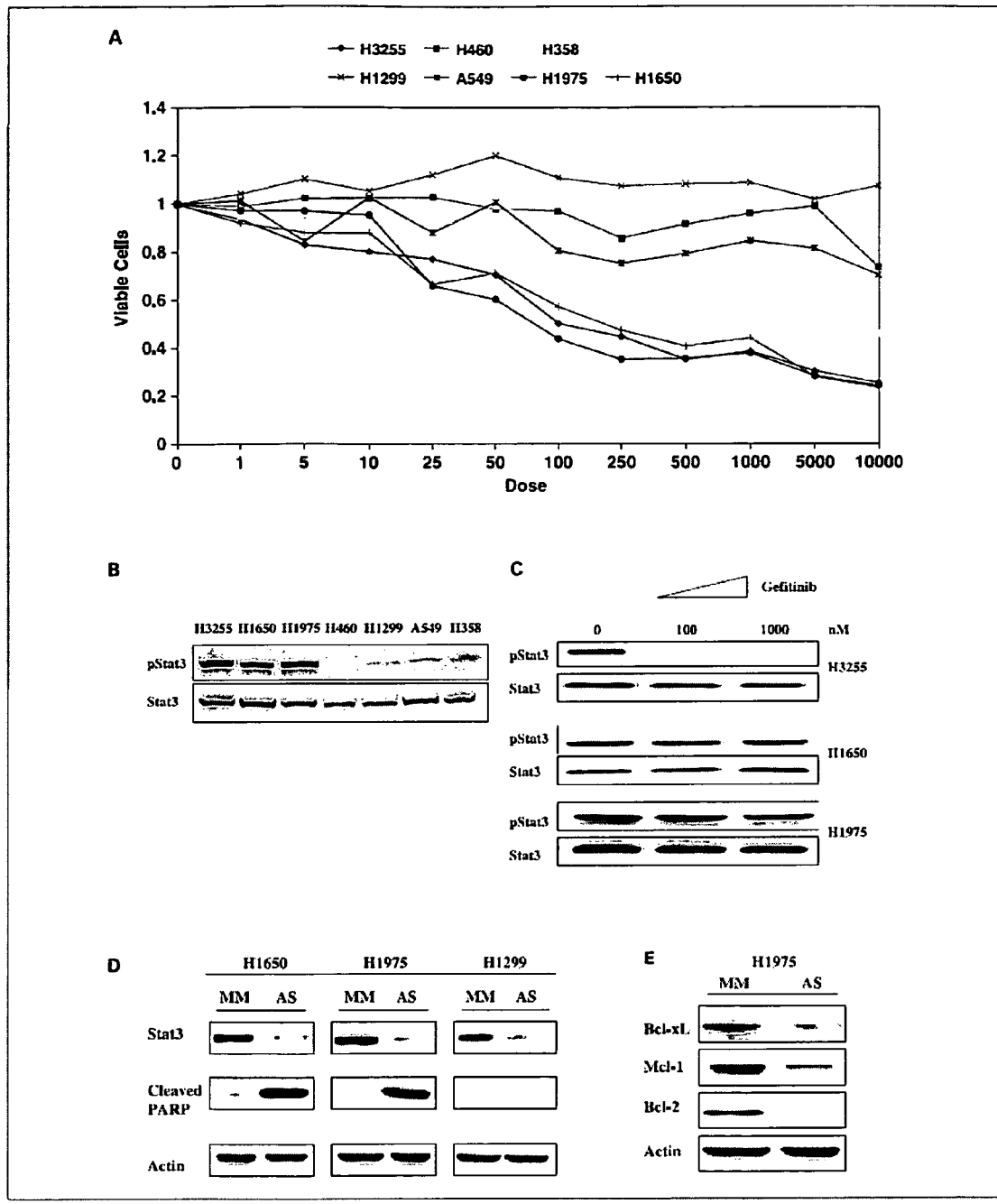
FIG. 9A is a graph demonstrating differential sensitivity of non-small cell lung cancer cell lines to gefitinib.
FIG. 9B is a photograph of a Western blot analysis for phosphorylated and total Stat3.
FIG. 9C is a photograph of a Western blot analysis for phosphorylated Stat3 and total Stat3 after treatment with increasing amounts of gefitinib.
FIG. 9D is a photograph of a Western blot analysis for Stat3, cleaved PARP and Actin after treatment with Stat3 antisense oligonucleotides (AS) or a mismatch control (MM).
FIG. 9E is a photograph of a Western blot analysis for the indicated apoptosis-related markers after treatment with Stat3 antisense oligonucleotides (AS) or a mismatch control (MM).

The level of activated Stat3 was assessed in cell lines harboring mutant EGFR and cell lines with wild-type EGFR. See Haura et al., Clin. Cancer Res. 11:8288-8294 (2005), which is incorporated herein by reference. H3255, H1650, and H1975 (cell lines that contain mutations of EGFR), along with H460, H358, H1299, and A549 (NSCLC cell lines with wild-type EGFR), were exposed to increasing concentrations of gefitinib and cell viability was assayed. As shown in FIG. 9A, mutant EGFR cells were sensitive to gefitinib with an approximate $IC_{50}$ of 100 nmol/L, whereas wild-type cell lines were resistant to gefitinib ($IC_{50}$>10 μmol/L). To confirm that gefitinib sensitivity correlated with increased Stat3 activation, whole cell proteins from untreated cells were evaluated for phosphorylated Stat3 and total Stat3. The mutation status and sensitivity of cell lines to gefitinib correlated with the level of whole cell phosphorylated Stat3 activity because H3255, H1650, and H1975 cells have markedly higher levels of phosphorylated Stat3 compared with the other cell lines (FIG. 9B).

To evaluate whether inhibition of EGFR tyrosine kinase activity by gefitinib affects downstream Stat3 activity, NSCLC cells with distinct EGFR mutations were exposed to increasing doses of gefitinib for 24 hours and total proteins were evaluated for phosphorylated Stat3 and total Stat3 (FIG. 9C). In H3255 cells with the L858R mutation in EGFR, inhibition of EGFR tyrosine kinase by gefitinib resulted in a complete inhibition of phosphorylated Stat3. This suggested that loss of Stat3 activity contributes to gefitinib-mediated apoptosis. However, in H1650 cells with the L746-p753 deletion mutation in EGFR or in gefitinib-sensitive H1975 cells, gefitinib had no effect on phosphorylated Stat3. Gefitinib inhibition of EGFR function was confirmed by analysis of pTyr 1068 EGFR levels. Phosphorylated EGFR was down-regulated in all the cells tested. Therefore, despite enhanced levels of phosphorylated Stat3 in cells harboring EGFR mutations, the ability of gefitinib to down-regulate Stat3 activity seemed to be cell line dependent.

To determine if Stat3 plays a role in survival in EGFR mutant cells, antisense Stat3 oligonucleotides were used to down-regulate Stat3 as described above. H1650 and H1975 cells exposed to antisense Stat3 show decreased Stat3 protein levels as well as cleavage of poly(ADP-ribose) polymerase indicative of apoptosis (FIG. 9D). No apoptosis was observed in H1299 cells despite Stat3 knock-down. Levels of the Bcl-2 family proteins Bcl-xL, Mcl-1, and Bcl-2 were reduced in cells treated with antisense Stat3 consistent with the known role of Stat3 in regulating these proteins (FIG. 9E). These results suggest that Stat3 communicates a survival signal from mutant EGFR to downstream survival proteins.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

It will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

We claim:

1. A method of predicting responsiveness of cancer cells to a chemotherapeutic agent, comprising:
   a) measuring the level of phosphorylated Stat3 in a cancer cell;
   b) comparing the level of phosphorylated Stat3 in the cancer cell to the level of phosphorylated Stat3 in a control, wherein the level in the cancer cell is increased or not increased compared to the level in the control; and
   c) predicting the responsiveness of the cancer cells to the chemotherapeutic agent based on the level of phosphorylated Stat3 in the cancer cell as compared to the level in the control, wherein when the level in the cancer cell is increased, it is indicative of responsiveness to tyrosine kinase inhibitors, and when the level in the cancer cell is not increased, it is indicative of responsiveness to chemotherapeutic agents that induce apoptosis.

2. The method of claim 1, wherein the cancer cell is obtained from a subject.

3. The method of claim 2, wherein the subject is human.

4. The method of claim 1, wherein the cancer cell is selected from the group consisting of a breast cancer cell, a lung cancer cell, an ovarian cancer cell, a head and neck cancer cell, a melanoma cell, a prostate cancer cell, a multiple myeloma cell, a lymphoma cell, a leukemia cell, a gastric cancer cell, an ovary cancer cell, a colon cancer cell, and a pancreatic cancer cell.

5. The method of claim 4, wherein the cancer cell is a breast cancer cell.

6. The method of claim 4, wherein the cancer cell is a non-small cell lung cancer cell.

7. The method of claim 1, wherein the chemotherapeutic agent is selected from the group consisting of alkylating agents, nitrosoureas, antimetabolites, anthracyclines, topoisomerase inhibitors, taxanes, vinca alkaloids, and tyrosine kinase inhibitors.

8. The method of claim 1, wherein the chemotherapeutic agent is a taxane.

9. The method of claim 8, wherein the taxane is docetaxel.

10. The method of claim 1, wherein the chemotherapeutic agent is a tyrosine kinase inhibitor.

11. The method of claim 10, wherein the tyrosine kinase inhibitor is selected from the group consisting of Stat inhibitors and EGFR inhibitors.

12. The method of claim 1, wherein the chemotherapeutic agent is doxorubicin.

13. The method of claim 1, wherein the level of phosphorylated Stat3 is increased in the cancer cell relative to the control and is predictive of responsiveness to tyrosine kinase inhibitors.

14. The method of claim 1, wherein the level of phosphorylated Stat3 is not increased in the cancer cell relative to the control and is predictive of responsiveness to chemotherapeutic agents that induce apoptosis.

15. The method of claim 1, wherein the cancer cell is obtained by a method selected from the group consisting of a biopsy and surgical resection.

16. The method of claim 1, wherein the level of phosphorylated Stat3 is measured by a method selected from the group consisting of immunohistochemistry, electrophoretic mobility shift assay, Western blot and ELISA.

17. The method of claim 1, wherein the predicted responsiveness is a complete pathologic response.

18. The method of claim 1, wherein the predicted responsiveness is a complete clinical response.

19. The method of claim 1, wherein the control is a non-cancerous cell.

20. The method of claim 19, wherein the non-cancerous cell is obtained from the same subject as the cancer cell.

21. The method of claim 1, wherein the control is a cancer cell.

22. The method of claim 1, wherein the control has a known responsiveness to chemotherapeutic agents.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Homo sapiens

<400> SEQUENCE: 1
gctccagcat ctgctgcttc            20

<210> SEQ ID NO 2
<211> LENGTH: 20
<212> TYPE: DNA

<213> ORGANISM: Homo sapiens

<400> SEQUENCE: 2
gctccaatac ccgttgcttc                                               20

<210> SEQ ID NO 3
<211> LENGTH: 24
<212> TYPE: DNA
<213> ORGANISM: Homo sapiens

<400> SEQUENCE: 3
agcttcattt cccgtaaatc ccta                                          24

<210> SEQ ID NO 4
<211> LENGTH: 20
<212> TYPE: DNA
<213> ORGANISM: Homo sapiens

<400> SEQUENCE: 4
cccagccttc cagctccttg                                               20

<210> SEQ ID NO 5
<211> LENGTH: 8
<212> TYPE: DNA
<213> ORGANISM: Homo sapiens
<220> FEATURE:
<221> NAME/KEY: misc_feature
<222> LOCATION: (3)..(6)
<223> OTHER INFORMATION: n is a, c, g, or t

<400> SEQUENCE: 5 ttnnnnaa                                                             8

<210> SEQ ID NO 6
<211> LENGTH: 9
<212> TYPE: DNA
<213> ORGANISM: Homo sapiens
<220> FEATURE:
<221> NAME/KEY: misc_feature
<222> LOCATION: (3)..(7)
<223> OTHER INFORMATION: n is a, c, g, or t

<400> SEQUENCE: 6 ttnnnnnaa                                                            9

<210> SEQ ID NO 7
<211> LENGTH: 20
<212> TYPE: DNA
<213> ORGANISM: Homo sapiens

<400> SEQUENCE: 7
cagtgagctg agatcatgcc                                               20

<210> SEQ ID NO 8
<211> LENGTH: 21
<212> TYPE: DNA
<213> ORGANISM: Homo sapiens

<400> SEQUENCE: 8
tattagccct ccagccccca c                                             21

<210> SEQ ID NO 9
<211> LENGTH: 31
<212> TYPE: DNA
<213> ORGANISM: Homo sapiens

```
-continued

<400> SEQUENCE: 9
tggagactca gtttcaaata aataaataaa c                              31

<210> SEQ ID NO 10
<211> LENGTH: 30
<212> TYPE: DNA
<213> ORGANISM: Homo sapiens

<400> SEQUENCE: 10
tgagttactg tattaaagaa tgggggcggg                                30

<210> SEQ ID NO 11
<211> LENGTH: 30
<212> TYPE: DNA
<213> ORGANISM: Homo sapiens

<400> SEQUENCE: 11
tgtggggaga ggttgcaaaa ataaataaat                                30
```